US008580940B2

(12) United States Patent
Tanaka et al.

(10) Patent No.: US 8,580,940 B2
(45) Date of Patent: Nov. 12, 2013

(54) PHOTOPORPHYRINOGEN OXIDASE HAVING ACTIVITY OF IMPARTING RESISTANCE AGAINST ACIFLUORFEN AND GENE THEREOF

(75) Inventors: Ayumi Tanaka, Hokkaido (JP);
Ryouichi Tanaka, Hokkaido (JP);
Kazushige Kato, Kanagawa (JP);
Takako Fukagawa, Kanagawa (JP)

(73) Assignees: Nippon Soda Co., Ltd., Tokyo (JP);
National University Corporation Hokkaido University, Hokkaido (JP)

( * ) Notice: Subject to any disclaimer, the term of this patent is extended or adjusted under 35 U.S.C. 154(b) by 0 days.

(21) Appl. No.: 13/358,564

(22) Filed: Jan. 26, 2012

(65) Prior Publication Data

US 2012/0184727 A1 Jul. 19, 2012

Related U.S. Application Data

(62) Division of application No. 12/088,141, filed as application No. PCT/JP2006/319001 on Sep. 25, 2006, now Pat. No. 8,129,589.

(30) Foreign Application Priority Data

Sep. 26, 2005 (JP) ................................ 2005-278942

(51) Int. Cl.
*C12N 15/09* (2006.01)
*C12N 15/31* (2006.01)
*C12N 15/52* (2006.01)
*C12N 15/65* (2006.01)

(52) U.S. Cl.
USPC .......... 536/23.7; 536/23.2; 435/471; 435/473

(58) Field of Classification Search
None
See application file for complete search history.

(56) References Cited

U.S. PATENT DOCUMENTS

2004/0019066 A1 1/2004 Danchin et al.

FOREIGN PATENT DOCUMENTS

| JP | 9-107833 A | 4/1997 |
|----|------------|--------|
| JP | 09-140381 | 6/1997 |
| JP | 11-346787 | 12/1999 |
| JP | 2000-270873 | 10/2000 |
| JP | 2000-312586 A | 11/2000 |
| WO | WO 00/71699 A1 | 11/2000 |
| WO | WO 01/36606 | 5/2001 |

OTHER PUBLICATIONS

Database EMBL, "*Synechocystis* sp. PCC 6803 DNA, complete genome," XP002513698, Dec. 9, 2004.

Database UniProt, "RecName:Full=UPF0093 membrane protein slr1790," XP002513697, Feb. 1, 1997.

Hihara et al., "A Novel Gene, pmgA, Specifically Regulates Photosystem Stoichiometry in the Cyanobacterium *Synechocystis* Species PCC 6803 in Response to High Light," Plant Physiol., 1998, 117:1205-1216.

Hoffman et al. "Transposome insertional mutagenesis and direct sequencing of microbial genomes," Genetica, 2000, 108:19-24.

Jansson, Christer, Use of *Synechocystis* 6803 to Study Expression of a psbA Gene Family, 1998, 297:166-183.

Jefferson et al., "GUS fusions: b-glucuronidase as a sensitive and versatile gene fusion marker in higher plants," The EMBO Journal, 1987, 6(13):3901-3907.

Kaneko et al,. "Sequence Analysis of the Genome of the Unicellular Cyanobacterium *Synechocystis* sp. Strain PCC6803. II. Sequence Determination of the Entire Genome and Assignment of Potential Protein-coding Regions," DNA Research, 1996, 3:109-136 (in Accession P72793).

Kumar et al., "High-Throughput Methods for the Large-Scale Analysis of Gene Function by Transposon Tagging," Methods in Enzymology, 2000, 328:550-574.

Kyozuka et al., "Effect of the promoter and the first intron of maize Adh1 on foreign gene expression in rice," Maydica, 1990, 35:353-357.

Lee et al., "Cellular Localization of Protoporphyrinogen-Oxidizing Activities of Etiolated Barley (*Hordeum vlugare* L.) Leaves," Plant Physiol, 1993, 102:881-889.

Lermontova et al,. "Overexpression of plastidic protoporphyrinogen IX oxidase leads to resistance to the diphenyl-ether herbicide acifluorfen," Plant Physiology, Jan. 2000, 122(1):75-84, XP002513705.

Murashige et al., "A Revised Medium for Rapid Growth and Bio Assays with Tobacco Tissue Cultures," Physiologia Plantarum, 1962, 15:473-497.

Nishibayashi et al., "Transformation of cucumber (*Cucumis sativus* L.) plants using *Agrobacterium tumefaciens* and regeneration from hypocotyl explants," Plant Cell Reports, 1996, 15:809-814.

Office Action dated Jun. 23, 2011, in corresponding Chinese application 201010541871.6, 1 page.

Randolph-Anderson et al., "Isolation and characterization of a mutant protoporphyrinogen oxidase gene from *Chlamydomonas reinhardtii* conferring resistance to prophyric herbicides," Plant Molecular Biology, Nov. 1, 1998, 38(5):839-859, XP002223975.

(Continued)

*Primary Examiner* — Russell Kallis
(74) *Attorney, Agent, or Firm* — Foley & Lardner LLP

(57) ABSTRACT

Protoporphyrinogen oxidase having an activity of imparting acifluorfen resistance and gene thereof are provided. Cyanobacterium protoporphyrinogen oxidase gene is identified by introducing a protoporphyrinogen oxidase gene of *Arabidopsis* into cyanobacterium, disrupting a cyanobacterium gene with a transposon, selecting a mutant strain in which protoporphyrinogen oxidase gene is disrupted, identifying the disrupted protoporphyrinogen oxidase gene, and isolating the disrupted protoporphyrinogen oxidase gene. This procedure is effective as a gene isolation technique when a protein derived from other organism species that is homologous to a known protein (e.g., protoporphyrinogen oxidase from cyanobacterium) can not be found in a gene database of the other species.

11 Claims, 5 Drawing Sheets

(56) References Cited

OTHER PUBLICATIONS

Sanger et al., "DNA sequencing with chain-terminating inhibitors," Proc. Natl. Acad. Sci. USA, Dec. 1977, 74(12):5463-5467.
Terada et al,. "Expression of CaMV35S-GUS gene in transgenic rice plants," Mol. Gene Genet., 1990, 220:389-392.
Toshiki et al., "Germline Transformation of the Silkworm *Bombyx mori* L. using a PiggyBac Transposon-Derived Vector," Nature Biotechnology, Jan. 2000, 18:81-84.
Uematsu et al., "*Agrobacterium*-Mediated Transformation and Regeneration of Kiwi Fruit," Plant Cell Reports, 1991, 10:286-290.
UPF0093 Membrane Protein slr1790—*Synechocystis* sp. (strain PCC 6803), UniProt/Swiss-Prot P72793 (Y1790_SYNY3), Feb. 1, 1997, www.uniprot.org/uniprot/P72793.
Vavilin et al., "Regulation of the tetrapyrrole biosynthetic pathway leading to heme and chlorophyll in plants and cyanobacteria," Physiologica Plantarum, 2002, 115:9-24.
Wang et al., "Application of transposon to screening of pigment-production genes of *Vibrio cholerae*," Bull. Acad. Mil. Med. Sci., Aug. 2005, 29(4):337-340, English abstract on first page.
Williams, John G.K., "Construction of Specific Mutations in Photosystem II Photosynthetic Reaction Center by Genetic Engineering Methods in *Synechocystis* 6803," Cyanobacteria, 1998, 167:766-778.

FIGURE 1

```
(SEQ ID NO:2)  Synechocystis_sp._PCC_6803        1:--------------MAYYWFKAFHLIGIVVWFAGLFYLVRLFVYHAEADQEPEPARTILK 46
(SEQ ID NO:21) Anabaena_sp._PCC_7120             1:----------------------------MVWFAGLFYLVRLFIYHVEANQEPEPARTILK 32
(SEQ ID NO:22) Gloeobacter_violaceus_PCC_7421    1:--------------MAYLWFKAFIITVGFVIWFAGLFYLVRLFIYHVEANEQPEAARAILK 46
(SEQ ID NO:23) Prochlorococcus_marinus_SS120     1:---------MSLPAESYLWLKTLHIIGVVVWFAGLFYLVRLFIYHVEADELESDIKFAFV 51
(SEQ ID NO:24) Prochlorococcus_marinus_MIT9313   1:---------MTFPPEAYLWFKTLHIVGVVVWFAGLFYLVRLFIYHVEAADLEPIVKKAFE 51
(SEQ ID NO:25) Synechococcus_sp._WH8102          1:---------MTLPPEAYLWFKTLHIVGVVVWFAGLFYLVRLFIYHVETAELAEDLQQPFR 51
(SEQ ID NO:26) Prochlorococcus_marinus_MED4      1:MVIVYELYFINLSSEAYLWFKSLHIIGVIVWFSGLFYLVRLFIYHEESRTMQDDLKIAFN 60
                                                                ........ ...  ....**.*********.**.*.    .   .

Synechocystis_sp._PCC_6803          47:KQYELMEKRLYNIITTPGMVVIVAMAIGLIFTEPEILKSGWLHIKLTFVALLLLYHFYCG 106
              Anabaena_sp._PCC_7120               33:NQYQIMEKRLYNIITTPGMLVIVAMAIGLVSTEPEVLKQGWLHFKLLCVALLLGYHHYCG 92
              Gloeobacter_violaceus_PCC_7421      47:KQYEIMEKRLLNIITTPGMVLTVAMAVGMLVVQPDWLKAGWLHIKLTLVVLLMGYHFYCM 106
              Prochlorococcus_marinus_SS120       52:NQYSIMERRLANIITTPGMIIAVSMAIGLLIYNPSWLEQIWMQVKLFFVFLLLIYHIFCY 111
              Prochlorococcus_marinus_MIT9313     52:EQYTIMERRLANIITTPGMIIAVSMAVGLLITQPSWINQAWMQAKLALVAGLIAYHIFCY 111
              Synechococcus_sp._WH8102            52:DQYSLMEKRLANIITTPGMVVAVSMAIGLLVAQPSWLQQGWMHAKLGFVAGLIAYHVACY 111
              Prochlorococcus_marinus_MED4        61:DQYSIMEKRLANIITTPGMILALSMAICLVIMQPGWLSEKWLQIKISFVLGLVIYHVYCY 120
                                                     **  .**.**.*********  ....**.... .*  .*..*.. *. .*..*.. ** .*.

Synechocystis_sp._PCC_6803         107:RVMKKLAQGESQWSGQQFRALNEAPTILLVVIVLLAVFKNNLPLDATTWLIVALVIAMAA 166
              Anabaena_sp._PCC_7120               93:RLMKKLAADECRWSSQQLRALNEAPTVMLVVTVMLAVFKNNLPTDLTAWLIFALIIFMAV 152
              Gloeobacter_violaceus_PCC_7421     107:RLRTQLAAGTCRWGPKQLRALNEAPTILLVTIVLLAVFKNDLPTDATAWIVFGLVISFAV 166
              Prochlorococcus_marinus_SS120      112:RIMSSLAKGECKWSGQQLRIINELPTLFLVIVVMLVVFKNNFPTSAATWLIVFLVIFMAL 171
              Prochlorococcus_marinus_MIT9313    112:RLMGQLNRGECSWSGRQLRAINELPTLFLVLVVMLVVFKNQFPTGAATWLIVGLVLFMAA 171
              Synechococcus_sp._WH8102           112:RLMGQLQAGTCRLSGKQLRALNELPTLLLVIVVMLVVFKSQFPTGAATWFIVALVVFMAA 171
              Prochlorococcus_marinus_MED4       121:KIMNSLQNGTSKISAKNLRLLNELPTLLLFVIVLLVIFKNNFPTSIATWSVFGLIIFMLL 180
                                                    ... *.  ...  ... ..*.***.**..*. .*.*..**...* ...*... *.....

Synechocystis_sp._PCC6803          167:SIQLYAKKRRRDQALLTEQQKAASAQN-                               193
              Anabaena_sp._PCC_7120              153:TIQLYAKKRRLDKEKLTAQIGQIPQEQS                               180
              Gloeobacter_violaceus_PCC_7421     167:TIQLYARKRRLDKEKQLASQGGQQ----                               190
              Prochlorococcus_marinus_SS120      172:SIQLYARFRRINKEKQI-----------                               188
              Prochlorococcus_marinus_MIT9313    172:SIQFYARWRRLRLSRQLESPINNG----                               195
              Synechococcus_sp._WH8102           172:SIQFYARWRRLRAFAQAVTGS-------                               192
              Prochlorococcus_marinus_MED4       181:SIQLYAKIRKKNEESLKNG---------                               199
                                                    .**.**. *..  . . 
```

FIGURE 2

```
(SEQ ID NO:2)   Synechocystis_sp._PCC_6803  1:---------------------MAYYWFKAFILIGIVVWFAGLFYLVRLFVYHAEADQE 37
(SEQ ID NO:27)  Pseudomonas_aeruginosa      1:----------------------MYMWLKAFHIIAVVCWFAGLFYLPRLFVYHAMSEDQ 36
(SEQ ID NO:28)  Helicobacter_pylori         1:------------------MGFLNGYFLWVKAFHVIAVISWMAALFYLPRLFVYHAFNAHK 42
(SEQ ID NO:29)  Agrobacterium_tumefaciens   1:MRAGVALGVFAAFIALLFYADPADLYLWIKALHIIAVISWMAAIFYLPRLFIYHTDAPVG 60
(SEQ ID NO:30)  Brucella_melitensis         1:----------MLGVWALFHVNPTDAYLWVKALHVIAVISWMAGMLYLPRLFVYHCSAQPG 50
                                                      ..* **.* *....*.*...**.***.**. .

Synechocystis_sp._PCC_6803  38:PEPAKTILKKQYEIMEKRLYNIITTPGMVVTVAMAIGLIFTEPEIL-KSGWLHIKLTFVA 96
                Pseudomonas_aeruginosa      37:TS------RERFCVMERKLYRGTMMPSMIATLVIGIWMLYLTPGWL-SQGWLHAKLTLVV 89
                Helicobacter_pylori         43:KE-----FVGVVQIQEKKLYSFIASPAMGFTLITGIIMLLIEPTLFKSGGWLHAKLALVV 97
                Agrobacterium_tumefaciens   61:SQ-----QSETFKVMEQRLIRVIMNPAMMISWTLGLYLAWSVYGFS--GGWLHAKIGLVL 113
                Brucella_melitensis         51:SV-----TSETFKVMEKRLLRFIINPAMVVTWITGLWMAWEIFGFQ--GGWLHAKLLLVV 103
                                                   .   ..*..*.. * *.*  .   ...  ..   .****.*. .*.

Synechocystis_sp._PCC_6803  97:LLLLYIIFYCGRVMKKLAQGESQWSGQQFRALNEAPTILLVVIVLLAVFKNNLPLDATIWL 156
                Pseudomonas_aeruginosa      90:LLIGYHHACGAMLKRFARGEPGRSHVFYRWFNEVPVLFLLLIVLLVVLKPF--------- 140
                Helicobacter_pylori         98:LLLAYHFYCKKCMRELEKDPTRRNARFYRVFNEAPTILMLIVILVVVKPF--------- 148
                Agrobacterium_tumefaciens   114:LLTATHVYFSRSAKRFARDENTRPARHWRLMNEVPTVLMILIVILVVVKPFG-------- 165
                Brucella_melitensis         104:LMSGVHGYLSKSTRIFAEDRNMSSAKHWRIINEVPTVLMILIVILAIVKPF--------- 154
                                                *.  .* ..   . .. ...   *  **.*. ....**.*...*..

Synechocystis_sp._PCC_6803  157:IVALVIAMVVSIQLYAKKRRRDQALLTEQQKAASAQN                  193
                Pseudomonas_aeruginosa      140:-------------------------------------                  140
                Helicobacter_pylori         148:-------------------------------------                  148
                Agrobacterium_tumefaciens   165:-------------------------------------                  165
                Brucella_melitensis         154:-------------------------------------                  154
```

PHOTOPORPHYRINOGEN OXIDASE HAVING ACTIVITY OF IMPARTING RESISTANCE AGAINST ACIFLUORFEN AND GENE THEREOF

CROSS-REFERENCE TO PRIOR RELATED APPLICATIONS

This application is a Divisional application of U.S. application Ser. No. 12/088,141, which is the U.S. national phase application under 35 U.S.C. §371 of International Patent Application No. PCT/JP2006/319001, filed Sep. 25, 2006, and claims the benefit of Japanese patent Application No. 2005-278942, filed Sep. 26, 2005, all of which are incorporated in their entirety by reference herein. The International Application was published in Japanese on Mar. 29, 2007, as International Publication No. WO 2007/034953 A1 under PCT Article 21(2).

The instant application contains a Sequence Listing which has been submitted in ANSI format via EFS-WEB and is hereby incorporated by reference in its entirety. Said ANSI copy, created on Jan. 24, 2012, is named sequence.txt and is 23 KB.

FIELD OF THE INVENTION

The present invention relates to protoporphyrinogen oxidases having an activity of imparting resistance against acifluorfen, and relates particularly to the protoporphyrinogen oxidases of cyanobacteria, genes thereof, transformants into which the gene is incorporated, etc.

BACKGROUND OF THE INVENTION

Protoporphyrinogen oxidase is an enzyme catalyzing the end stage reaction of heme synthesis and chlorophyll synthesis, i.e., it catalyzes the reaction that removes six electrons from protoporphyrinogen IX to synthesize protoporphyrin IX. Heme is a cofactor of heme proteins such as hemoglobin and cytochrome, and is an essential molecule for respiration, energy metabolism, and defense against oxygen stress. Heme synthetic pathway commonly exists in microorganisms, plants, and animals, and synthesizes heme from a precursor δ-aminolevulinic acid. Further, in plants, synthetic pathways of heme and chlorophyll share common steps from the precursor δ-aminolevulinic acid until protoporphyrin IX. Protoporphyrinogen oxidase is considered to play a regulatory role in this synthetic pathway. In land plants, the enzyme protoporphyrinogen oxidase, which is responsible for the chlorophyll metabolic system, can be a target enzyme for diphenyl ether (hereinafter referred to as DPE in some cases) herbicides. When DPE herbicides inhibit protoporphyrinogen oxidase activity, protoporphyrinogen IX, a substrate of the enzyme, will accumulate in chloroplast, and eventually the protoporphyrinogen IX will leak out to cytosol where it is oxidized to protoporphyrin IX by peroxidase. When exposed to light and oxygen, protoporphyrin IX may produce singlet oxygen and even other reactive oxygen species. Lipid peroxidation and entailing membrane damage results in rapid death of plant cells (Lee et al., 1993, Plant Physiol., 102, 881). On the other hand, cyanobacteria are known to be able to survive in the presence of DPE herbicide, although the reason or mechanism therefor is not known at all.

Protoporphyrinogen oxidase genes have already been isolated from several organisms. For example, Tobacco PPX1 gene (Genbank accession Y13465) and PPX2 gene (Genbank accession Y13466), *Arabidopsis thaliana* PPOX gene (Genbank accession D83139), *Bacillus subtilis* HemY gene (Genbank accession M97208), mouse PPX gene (Genbank accession D45185), human PPX gene (Genbank accession D38537), *Saccharomyces cerevisiae* PPX gene (Genbank accession Z71381), *Escherichia coli* hemG gene (Genbank accession X68660) are known.

As an application of protoporphyrinogen oxidases, for example, Japanese Patent Application No. 09-107833 discloses a method to express a protoporphyrinogen oxidase from *Bacillus subtilis*, which confers resistance against DPE herbicides in a plant and discloses a transgenic plant expressing said protoporphyrinogen oxidase. Further, for example, in Japanese Laid-Open Patent Application No. 09-140381, a protoporphyrinogen oxidase gene of 1.7 kbp length obtainable from *Arabidopsis* is disclosed as a gene of an enzyme protein in porphyrin biosynthesis system, wherein the gene is suitable for plant cultivation and contains the restriction enzyme EcoR1 recognition nucleotide sequence (5'-GAATTC-3') at the site 1.3 kbp from its 5' end. Furthermore, for example, Japanese Patent Application No. 11-346787 discloses a simple method for evaluating inhibitory activity against protoporphyrinogen oxidase derived from rat or *Chlamydomonas*, said method including the steps of: (1) culturing transformants, which are generated by introducing a DNA fragment composed of operably linked promoter being operable in a host cell and a protoporphyrinogen oxidase gene into a host cell that is deficient in protoporphyrinogen oxidase activity-based growth, and are expressing the protoporphyrinogen oxidase gene present on the DNA fragment, in a medium in the presence or absence of a test compound and measuring the growth rate of the transformants under each condition, wherein the medium does not substantially contain a compound that complements the deficiency in protoporphyrinogen oxidase activity-based growth; and (2) determining the inhibitory activity of the test compound against protoporphyrinogen oxidase activity by determining the degree of inhibition on the transformants' growth via contact with the test compound based on the difference in growth.

On the other hand, in cyanobacteria, a gene analogous to *E. coli* hemK was speculated to be protoporphyrinogen oxidase from analysis of its gene database. Later, however, said hemK analogous gene of cyanobacteria was proved not to be protoporphyrinogen oxidase in fact. However, proteins homologous to protoporphyrinogen oxidases of other species ever identified have not been found in cyanobacteria gene database, and cyanobacteria protoporphyrinogen oxidase has not been isolated yet (see, e.g., Dmitrii V. Vavilin, Wim F. J. Vermaas, Regulation of the tetrapyrrole biosynthetic pathway leading to heme and chlorophyll in plants and cyanobacteria, Physiologia Plantarum, Vol. 115, p. 9, 2002).

SUMMARY OF THE INVENTION

As described above, proteins homologous to known protoporphyrinogen oxidases from other species have not been found in the cyanobacteria gene database, and cyanobacteria protoporphyrinogen oxidase has not been isolated so far. An object of the present invention is to provide a protoporphyrinogen oxidase having an activity of imparting acifluorfen resistance and gene thereof, and a transformant into which said gene is incorporated, etc.

The present inventors tried complementation screening using protoporphyrinogen oxidase-deficient *E. coli* with the aim of isolating protoporphyrinogen oxidase from cyanobacterium. In this method, a genomic fragment from cyanobacteria is introduced into protoporphyrinogen oxidase-deficient E. coli and a gene that complements the deficiency is searched to identify the gene relating to oxidation of protoporphyrinogen IX in cyanobacteria. Protoporphyrinogen oxidase genes derived from *Arabidopsis* and Tobacco were isolated by the same method using a different vector. Outline of the complementation screening will be described below.

First, DNA was obtained from a cyanobacterium (*Synechocystis* PCC6803). A phage vector λZaPII (STRATEGENE) was employed for DNA library construction. Since the complete nucleotide sequence of said cyanobacterium was already reported (approximately 3,500 kb), the cyanobacterium genome sequence was investigated for the six restriction enzyme sequences contained in the multicloning site of the vector. Three enzymes, XbaI, SpeI, and EcoRI, were considered appropriate for library construction. Accordingly, a phage library was constructed based on treatment with these three restriction enzymes. Complementation experiment was carried out by introducing the resulting library into a protoporphyrinogen oxidase-deficient *E. coli* and testing protoporphyrinogen oxidase activity of the transformants. Clear complementation, however, was not observed. Several possibilities were conceivable from this result: for example, the cyanobacterium protoporphyrinogen oxidase gene unfortunately carries sequences of these three restriction enzymes or a promoter of said cyanobacterium did not function well, etc.

Therefore, another library was constructed using limited digestion with the restriction enzyme Tsp509I and was reexamined. Tsp509I is a four-base recognition restriction enzyme. Since the restriction enzymes used in the previous attempt to construct the library (EcoRI, SpeI, and XbaI) recognize six-base sequences, it can not be avoided to generate fragments of too large a size. Furthermore, if the recognition site of these restriction enzymes exists within the cyanobacterium protoporphyrinogen oxidase gene sequence, a full-length protoporphyrinogen oxidase gene cannot be cloned. On the other hand, complete digestion of DNA with a four-base recognition restriction enzyme produces a large number of short fragments of several hundreds bp. To solve this problem, DNA was digested incompletely (limited digestion) with the four-base recognition restriction enzyme to construct a library. Even with this library, protoporphyrinogen oxidase deficiency in *E. coli* was not complemented.

Next, the present inventors thought that plasmid form might restore the growth and excised a large quantity of plasmids from the Tsp509I cyanobacterium genomic phage library to construct the Tsp509I cyanobacterium genomic plasmid library for investigation. However, remarkable growth restoration was not observed in any clone. From this result, it was thought that cyanobacterium protoporphyrinogen oxidase does not complement *E. coli* protoporphyrinogen oxidase deficiency or the complementation is, if any, very slight.

Then, the present inventors conducted intensive study to solve the above problem. Based on the knowledge that cyanobacteria have acifluorfen resistance, the present inventors employed a cyanobacterium mutant screening using a transposon, leading to isolation of porphyrinogen oxidase from a cyanobacterium (*Synechocystis* PCC6803) for the first time, found that the porphyrinogen oxidase had an activity of imparting acifluorfen resistance, and identified the gene thereof, attaining the present invention. Further, the present invention has been completed with the finding that the gene screening procedure using the transposon is a useful method for isolating a gene when a protein of other species homologous to a known protein can not be found in a gene database of the other species.

In other words, the present invention relates to: a protoporphyrinogen oxidase having an activity of imparting acifluorfen resistance to an organism and being derived from cyanobacterium; the protoporphyrinogen oxidase described above, wherein cyanobacterium is a cyanobacterium belonging to the genus *Synechocystis*; and the protoporphyrinogen oxidase according to either of the above, wherein the organism is a plant.

The present invention also relates to a protein shown in any one of the following: a protein containing the amino acid sequence shown in SEQ ID NO: 2; a protein having protoporphyrinogen oxidase activity, which contains an amino acid sequence wherein one or several amino acids are deleted, substituted, or added in the amino acid sequence shown in SEQ ID NO: 2, and which has an activity of imparting acifluorfen resistance to an organism; and a protein having protoporphyrinogen oxidase activity, which has 20% or more homology to the amino acid sequence shown in SEQ ID NO: 2, and has an activity of imparting acifluorfen resistance to an organism. It also relates to the protein described above, wherein the protein is derived from cyanobacterium.

The present invention also relates to a protoporphyrinogen oxidase gene DNA encoding the protoporphyrinogen oxidase described above or encoding the protein described above, and a protoporphyrinogen oxidase gene DNA shown in either of the following: a protoporphyrinogen oxidase gene DNA containing the nucleotide sequence shown in SEQ ID NO: 1; or a protoporphyrinogen oxidase gene DNA that contains a nucleotide sequence wherein one or several nucleotides are deleted, substituted, or added in SEQ ID NO: 1, and encodes a protein having protoporphyrinogen oxidase activity and having an activity of imparting acifluorfen resistance to an organism. It also relates to: a protoporphyrinogen oxidase gene DNA that hybridizes with a DNA containing a sequence complementary to the nucleotide sequence shown in SEQ ID NO: 1 under stringent conditions and encodes a protein having protoporphyrinogen oxidase activity and having an activity of imparting acifluorfen resistance to an organism; and the protoporphyrinogen oxidase gene DNA described above, wherein the protein having protoporphyrinogen oxidase activity is derived from a cyanobacterium.

The present invention also relates to a recombinant vector into which the protoporphyrinogen oxidase gene DNA described above is incorporated.

The present invention also relates to: a transformant into which the recombinant vector described above is introduced; the transformant described above, wherein the transformant has a resistance to acifluorfen; the transformant described above, wherein the transformant is a microorganism; the transformant according to either of the first two descriptions above, wherein the transformant is a plant; and the transformant according to the last description, wherein photosynthetic capacity is increased.

The present invention also relates to: a method for evaluating an inhibitory activity against protoporphyrinogen oxidase using the transformant described above; and a screening method for a protoporphyrinogen oxidase inhibitor using the transformant described above.

The present invention also relates to a method for isolating a cyanobacterium protoporphyrinogen oxidase gene, including the steps of: introducing an *Arabidopsis* protoporphyrinogen oxidase gene into cyanobacterium; disrupting a cyanobacterium gene by using a transposon; selecting a protoporphyrinogen oxidase gene-disrupted mutant strain; identifying the disrupted protoporphyrinogen oxidase gene; and isolating the disrupted protoporphyrinogen oxidase gene.

The present invention also relates to: a method for using the protein described above as protoporphyrinogen oxidase; a method for converting protoporphyrinogen IX into protoporphyrin IX by artificially contacting the protoporphyrinogen IX with the protein described above; a method for using the DNA described above as a protoporphyrinogen oxidase gene; and a method for converting protoporphyrinogen IX into protoporphyrin IX by contacting the protoporphyrinogen IX with an expression product artificially expressed from the DNA described above.

The present invention also relates to a method for isolating a gene encoding a protein having a certain function from a specific organism, including the steps of:

generating a transformant by introducing into the specific organism a gene encoding a protein complementing the certain function, wherein the gene is derived from an organism other than the specific organism;

generating a mutant strain of the transformant by randomly disrupting a gene of the transformant;

selecting a mutant strain disrupted in the gene encoding the protein having the certain function either by using an agent that acts on the protein complementing the certain function but does not act on the protein having the certain function or by changing culture conditions;

identifying the disrupted gene encoding the protein having the certain function; and isolating the disrupted gene encoding the protein having the certain function.

The present invention also relates to: the method for isolating a gene described above, wherein the mutagenesis is a mutagenesis using a transposon; the method for isolating a gene described above, wherein the protein complementing the certain function derived from an organism other than the specific organism is *Arabidopsis* protoporphyrinogen oxidase; the method for isolating a gene according to the last description, wherein the agent that acts on the protein complementing the certain function but does not act on the protein having the certain function is acifluorfen; and the method for isolating a gene according to either of the last two descriptions, wherein the protein having a certain function in the specific organism is cyanobacterium protoporphyrinogen oxidase.

BRIEF DESCRIPTION OF THE DRAWINGS

FIG. 1 shows alignment of the amino acid sequence of SEQ ID NO: 2 and amino acid sequences encoded by genes with unknown function derived from cyanobacteria.

FIG. 2 shows alignment of the amino acid sequence of SEQ ID NO: 2 and amino acid sequences encoded by genes with unknown function derived from other organisms.

DETAILED DESCRIPTION OF THE INVENTION

Figure 3:
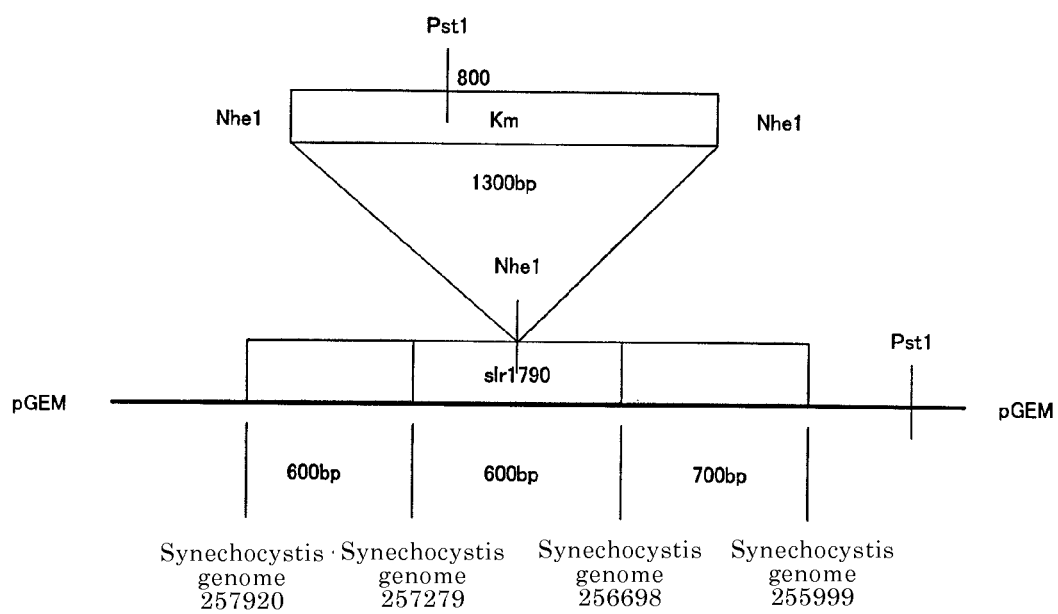
FIG. 3 is a figure showing a construct for disruption of *Synechocystis* slr1790 gene (pslr1790SKM, 6.4 kb).

Protoporphyrinogen oxidase of the present invention has an activity of imparting acifluorfen resistance to an organism. The "protoporphyrinogen oxidase having an activity of imparting acifluorfen resistance to an organism" herein means a protoporphyrinogen oxidase that increases acifluorfen resistance of the organism when the protoporphyrinogen oxidase is introduced into an appropriate organism and appropriately expressed in the organism. The increase in acifluorfen resistance of the organism can be evaluated by, for example, investigating whether LC 50 value of acifluorfen to the organism is increased at 48 hours after the enzyme introduction compared with the value before the enzyme introduction. Particularly, when the organism is a plant, increase in acifluorfen resistance of the plant can be investigated by, for example, confirming decrease in degree of etiolation, browning, or desiccation in the plant appropriately expressing the enzyme, compared with the plant before the appropriate expression of the enzyme when a particular amount of acifluorfen is applied to the cultivation soil, or it can be investigated by confirming increase in amount of acifluorfen application per unit of area required to cause the same degree of etiolation, browning, or desiccation in the plant appropriately expressing the enzyme, compared with the plant before the appropriate expression of the enzyme. Further, degree of improvement in acifluorfen resistance is not particularly limited but it is preferred to be an increase of preferably 1.1 times or more, more preferably 1.5 times or more, even more preferably 2 times or more, most preferably 3 times or more, either in LC 50 value of acifluorfen against the organism at 48 hours later or in amount of acifluorfen application per unit area required to cause the same level of etiolation, browning, or desiccation than that before the enzyme introduction.

Further, the "protoporphyrinogen oxidase having an activity of imparting acifluorfen resistance to an organism" of the present invention includes the case where the protoporphyrinogen oxidase itself has acifluorfen resistance. Herein, the term "the protoporphyrinogen oxidase itself has acifluorfen resistance" means that the specific activity of protoporphyrinogen oxidase in an appropriate solvent containing 1 μM of acifluorfen remains one fiftieth or higher, preferably one twentieth or higher, and more preferably one tenth or higher than that in the absence of acifluorfen. The term "protoporphyrinogen oxidase activity" herein means an enzymatic activity to oxidize protoporphyrinogen IX to protoporphyrin IX. Specific activity of protoporphyrinogen oxidase of a protein can be easily checked by, for example, contacting the protein with protoporphyrinogen IX in an appropriate buffer or salt solution and examining the yield of protoporphyrin IX. Further, the "organism" in the phrase "having an activity of imparting acifluorfen resistance to an organism" is not particularly limited and it may be a plant or a microorganism. However, a plant is preferred. Among plants, *Arabidopsis*, tobacco, maize, rice, family of wheat (such as wheat and barley), and potatoes (such as white potatoes) are preferred.

The protoporphyrinogen oxidase of the present invention may be or may not be from cyanobacteria as long as it has an activity of imparting acifluorfen resistance to an organism. Examples of cyanobacteria include, but are not limited to, cyanobacteria belonging to the genera *Synechocystis, Anabaena, Gloeobacter, Prochlorococcus, Synechococcus,* and *Rhodopseudomonas*, and more specifically, *Synechocystis* PCC6803, Anabaena PCC7120, *Gloeobacter violaceus* PCC7421, *Prochlorococcus marinus* SS120, *Prochlorococcus marinus* MIT9313, *Prochlorococcus marinus* MED4, *Synechococcus* WH8102, and *Rhodopseudomonas palustris*. Among these, cyanobacteria belonging to the genus *Synechocystis* is preferred, and *Synechocystis* PCC6803 is more preferred.

The term "protoporphyrinogen oxidase derived from cyanobacterium" herein includes, in addition to protoporphyrinogen oxidase actually existing in cyanobacterium, protoporphyrinogen oxidase expressed in a microorganism, etc., other than cyanobacterium by using recombinant techniques, etc., as long as it is the same as the protoporphyrinogen oxidase actually existing in cyanobacterium.

A protein of the present invention is any one of the following proteins: (1) a protein containing the amino acid sequence shown in SEQ ID NO: 2; (2) a protein having an activity of imparting acifluorfen resistance to an organism, having protoporphyrinogen oxidase activity, and containing an amino acid sequence in which one or several amino acids are deleted, substituted, or added in any of (i) the amino acid sequence shown in SEQ ID NO: 2, (ii) the amino acid sequences of amino acid positions 1 to 34 and 48 to 176 of SEQ ID NO: 2, or (iii) the amino acid sequences of amino acid positions 1 to 34 and 48 to 193 of SEQ ID NO: 2; and (3) a protein having an activity of imparting acifluorfen resistance to an organism, having protoporphyrinogen oxidase activity, and having a homology of 20% or more to any of (i) the amino acid sequence shown in SEQ ID NO: 2, (ii) the amino acid sequences of amino acid positions 1 to 34 and 48 to 176 of SEQ ID NO: 2, or (iii) the amino acid sequences of amino acid positions 1 to and 48 to 193 of SEQ ID NO: 2. Hereinafter, these proteins of the present invention may be collectively referred to as "the present protein(s)."

The protein of above (2) of the present invention is not particularly limited as long as it is a protein having an activity of imparting acifluorfen resistance to an organism, having protoporphyrinogen oxidase activity, and containing an amino acid sequence in which one or several amino acids are deleted, substituted, or added in any one of (i) the amino acid sequence shown in SEQ ID NO: 2, (ii) the amino acid sequences of amino acid positions 1 to 34 and 48 to 176 of SEQ ID NO: 2, or (iii) the amino acid sequences of amino acid positions 1 to 34 and 48 to 193 of SEQ ID NO: 2. However, preferred examples include: a protein having an activity of imparting acifluorfen resistance to an organism, having protoporphyrinogen oxidase activity, and containing an amino acid sequence in which one or several amino acids are deleted, substituted, or added in the amino acid sequence shown in SEQ ID NO: 2; a protein having an activity of imparting acifluorfen resistance to an organism, having protoporphyrinogen oxidase activity, containing an amino acid sequence in which one or several amino acids are deleted, substituted, or added in the amino acid sequences of amino acid positions 1 to 34 and 48 to 176 of SEQ ID NO:2, and containing an amino acid sequence composed of any 10 to 16, preferably any 12 to 14, and more preferably any 13 amino acids between an amino acid sequence corresponding to said amino acid sequence of amino acid positions 1 to 34 and an amino acid sequence corresponding to said amino acid sequence of amino acid positions 48 to 176; and a protein having an activity of imparting acifluorfen resistance to an organism, having protoporphyrinogen oxidase activity, containing an amino acid sequence in which one or several amino acids are deleted, substituted, or added in the amino acid sequence of amino acid positions 1 to 34 and 48 to 193 of SEQ ID NO:2, and containing an amino acid sequence composed of any 10 to 16, preferably any 12 to 14, and more preferably any 13 amino acids between an amino acid sequence corresponding to said amino acid sequence of amino acid positions 1 to 34 and an amino acid sequence corresponding to said amino acid sequence of amino acid positions 48 to 193. Herein, an amino acid sequence corresponding to the amino acid sequence of amino acid positions m to n means an amino acid sequence in which one or several amino acids are deleted, substituted, or added in the amino acid sequence of amino acid position m to n.

The above "amino acid sequence in which one or several amino acids are deleted, substituted, or added" means an amino acid sequence in which any number of amino acids, for example, 1 to 20, preferably 1 to 15, more preferably 1 to 10, even more preferably 1 to 5, and most preferably 1 to 3 amino acids are deleted, substituted, or added.

The term "having protoporphyrinogen oxidase activity" herein means having an enzyme activity to oxidize protoporphyrinogen IX to protoporphyrin IX. Presence of the protoporphyrinogen oxidase activity in a protein can be easily confirmed by evaluating the production of protoporphyrin IX after contacting the protein with protoporphyrinogen IX in an appropriate buffer or salt solution.

Further, the "protein having an activity of imparting acifluorfen resistance to an organism" herein means a protein which increases acifluorfen resistance of the organism when the protein is introduced into an appropriate organism and appropriately expressed in the organism. Increase in acifluorfen resistance of the organism can be evaluated by, for example, investigating whether LC 50 value of acifluorfen to the organism is increased at 48 hours after the protein introduction compared with the value before the protein introduction. Further, particularly when the organism is a plant, increase in acifluorfen resistance of the plant can be investigated by, for example, confirming decrease in degree of etiolation, browning, or desiccation in the plant appropriately expressing the protein in the plant, compared with the plant before the appropriate expression of the protein when a particular amount of acifluorfen is applied to the cultivation soil, or it can be investigated by confirming increase in amount of acifluorfen application per unit of area required to cause the same degree of etiolation, browning, or desiccation in the plant appropriately expressing the protein, compared with the plant before the appropriate expression of the protein. Further, degree of improvement in acifluorfen resistance is not particularly limited but it is preferred to be an increase by preferably 1.1 times or more, more preferably 1.5 times or more, even more preferably 2 times or more, and most preferably 3 times or more either in LC 50 value of acifluorfen to the organism 48 hours later or in amount of acifluorfen application per unit area required to cause the same level of etiolation, browning, or desiccation than that before the protein introduction.

Further, the "protein having an activity of imparting acifluorfen resistance to an organism" of the present invention includes the case where the protein itself has acifluorfen resistance. Herein, "the protein itself has acifluorfen resistance" means that a specific activity (relating to protoporphyrinogen oxidase activity) of the protein in an appropriate solvent containing 1 μM of acifluorfen is preferably one fiftieth or higher, more preferably one twentieth or higher, or more preferably one tenth or higher than a specific activity (relating to protoporphyrinogen oxidase activity) of the protein in the absence of acifluorfen. The term "protoporphyrinogen oxidase activity" herein means an enzymatic activity to oxidize protoporphyrinogen IX to protoporphyrin IX. Specific activity (relating to protoporphyrinogen oxidase) of a protein can be easily confirmed by, for example, contacting the protein with protoporphyrinogen IX in an appropriate buffer or salt solution and examining the yield of protoporphyrin IX. Further, the "organism" in the expression "having an activity of imparting acifluorfen resistance to an organism" is not particularly limited but plants and microorganisms are preferred. Particularly preferred are plants.

The above protein (3) of the present invention is not particularly limited as long as it is a protein having an activity of imparting acifluorfen resistance to an organism, having protoporphyrinogen oxidase activity, and having a homology of 20% or more to any of (i) the amino acid sequence shown in SEQ ID NO: 2 (slr1790), (ii) the amino acid sequences of amino acid positions 1 to 34 and 48 to 176 of SEQ ID NO: 2, or (iii) the amino acid sequences of amino acid positions 1 to 34 and 48 to 193 of SEQ ID NO: 2. However, the homology to any of (i) the amino acid sequence shown in SEQ ID NO: 2, (ii) the amino acid sequences of amino acid positions 1 to 34 and 48 to 176 of SEQ ID NO: 2, or (iii) the amino acid sequences of amino acid positions 1 to 34 and 48 to 193 of SEQ ID NO: 2 should preferably be 45% or more, more preferably 54% or more, even preferably 65% or more, further more preferably 80% or more, even more preferably 90% or more, and most preferably 95% or more. The term "homology to the amino acid sequences of amino acid positions o to p and q to r is X % or more" herein means that the homology is X % or more to an amino acid sequence containing amino acid sequences of amino acid positions o to p and amino acid positions q to r in this order, between which an amino acid sequence composed of any 10 to 16, preferably 12 to 14, or more preferably 13 amino acids is contained. The "protein having an activity of imparting acifluorfen resistance to an organism" and "protein having an activity of imparting acifluorfen resistance to an organism" in the protein of above (3) and their preferable embodiments have the same meaning as that of the protein of above (2).

In addition, BLAST-based search for proteins with high homology to the amino acid sequence shown in SEQ ID NO: 2 revealed several genes of unknown function encoding amino acid sequences having high homology to the amino acid sequence shown in SEQ ID NO: 2. Among these, cyanobacteria-derived genes of unknown function are shown in the below Table 1. Also shown in Table 1 is homology (%) of the amino acid sequences encoded by these genes to the amino acid sequence shown in SEQ ID NO: 2. These are also encompassed by the present proteins. Meanwhile, the amino acid sequence of the present invention shown in SEQ ID NO: 2 is the amino acid sequence encoded by the *Synechocystis* PCC6803-derived slr1790 gene, which has been revealed by the present inventors as described in the below Examples.

TABLE 1

| Genus of cyanobacteria | Genes | Homology to the slr1790 amino acid sequence |
|---|---|---|
| Synechocystis sp. PCC6803 | slr1790 | — |
| Anabaena sp. PCC7120 | alr5217 | 68 |
| Gloeobacter violaceus PCC7421 | gll3040 | 65 |
| Prochlorococcus marinus SS120 | Pro0955 | 55 |
| Prochlorococcus marinus MIT9313 | PMT0725 | 54 |
| Synechococcus sp. WH8102 | SYNW1243 | 56 |
| Prochlorococcus marinus MED4 | PMM0881 | 46 |
| Rhodopseudomonas palustris | RPA0297 | 27 |

Further, alignment of the amino acid sequences encoded by the genes set forth in Table 1 is shown in the below FIG. 1.

In the FIG. 1 alignment, an asterisk is added under the amino acids identical in all the 7 genes, while a dot is added under the amino acids identical in 4 to 6 genes. As can be understood from Table 1 and FIG. 1, these amino acid sequences of 7 cyanobacteria (exclusive of *Synechocystis* PCC6803) have high homology to the amino acid sequence encoded by the *Synechocystis* PCC6803 slr1790 gene and certain regions are highly conserved. Therefore, the proteins encoded by these genes in addition to the *Synechocystis* PCC6803 slr1790 gene are estimated to be protoporphyrinogen oxidases having an activity of imparting acifluorfen resistance to organisms as with the protein encoded by the *Synechocystis* PCC6803 slr1790 gene (the amino acid sequence of SEQ ID NO: 2). In addition, the alignment of the FIG. 1 shows high conservation of the protoporphyrinogen oxidase of the present invention in the amino acid sequences of amino acid positions 1 to 34 and 48 to 193 of the amino acid sequence of SEQ ID NO: 2 (corresponding to the nucleotide sequences of nucleotide positions 1 to 102 and 142 to 582) and especially the amino acid sequences of amino acid positions 1 to 34 and 48 to 176 of the amino acid sequence of SEQ ID NO: 2 (corresponding to the nucleotide sequences of nucleotide positions 1 to 102 and 142 to 528) among the amino acid sequence of SEQ ID NO: 2 or the nucleotide sequence of SEQ ID NO: 1. Thus, these regions are also likely to play an important role in the property of said enzymes.

Further, among the genes shown by the BLAST search to encode an amino acid sequence having a high homology to the amino acid sequence of SEQ ID NO: 2, genes from organisms other than cyanobacteria are shown in the below Table 2. The present proteins also include expression products of these genes.

TABLE 2

| Organism species | Gene | Homology to the slr1790 amino acid sequence (%) |
|---|---|---|
| Synechocystis sp. PCC6803 | slr1790 | — |
| Pseudomonas aeruginosa | PA0661 | 35 |
| Helicobacter pylori | O26018 | 33 |
| Brucella melitensis | Q8YJTO | 29 |
| Agrobacterium tumefaciens (strain C58/ATCC33970) | Q8UBL7 | 25 |

Further, alignment of the amino acid sequences encoded by the genes shown in Table 2 is shown in FIG. 2.

In the FIG. 2 alignment, an asterisk is added under the amino acids identical in all the 5 genes, while a dot is added under the amino acids identical in 3 genes. As can be understood from Table 2 and FIG. 2, these amino acid sequences of 4 species (exclusive of *Synechocystis* PCC6803) have high homology to the amino acid sequence encoded by the *Synechocystis* PCC6803 slr1790 gene and certain regions are highly conserved. Therefore, the proteins encoded by these genes in addition to the *Synechocystis* PCC6803 gene are also estimated to be protoporphyrinogen oxidases having an activity of imparting acifluorfen resistance to an organism as with the protein encoded by the *Synechocystis* PCC6803 slr1790 gene.

The present invention also relates to a method for using the present proteins above as protoporphyrinogen oxidase. The "use as protoporphyrinogen oxidase" herein means, for example, use of the present protein in a reaction in which the reaction product protoporphyrin IX is produced by artificially contacting the present protein with the substrate protoporphyrinogen IX in vitro or in vivo. The finding that the present proteins have protoporphyrinogen oxidase activity is a whole new finding first shown in the present invention. Further, the term "artificially contacting" in the method for converting protoporphyrinogen IX into protoporphyrin IX by artificially contacting protoporphyrinogen IX with the present protein means an artificial contact in vitro or in vivo and does not include, for example, a non-artificial contact in a cyanobacteria) cell.

The protoporphyrinogen oxidase gene DNA of the present invention is any of the following protoporphyrinogen oxidase gene DNA: (1) a protoporphyrinogen oxidase gene DNA encoding the protoporphyrinogen oxidase of the present invention or the present proteins; (2) a protoporphyrinogen oxidase gene DNA containing the nucleotide sequence shown in SEQ ID NO: 1; (3) a protoporphyrinogen oxidase gene DNA that encodes a protein having protoporphyrinogen oxidase activity and having an activity of imparting acifluorfen resistance to an organism, and contains a nucleotide sequence in which one or several nucleotides are deleted, substituted, or added in any one of (i) the nucleotide sequence shown in SEQ ID NO: 1, (ii) the nucleotide sequences of nucleotide positions 1 to 102 and 142 to 528 of SEQ ID NO: 1, or (iii) the nucleotide sequences of nucleotide positions 1 to 102 and 142 to 582 of SEQ ID NO: 1; and (4) a protoporphyrinogen oxidase gene DNA that encodes a protein having an activity of imparting acifluorfen resistance to an organism and having protoporphyrinogen oxidase activity, and hybridizes under straight conditions with a DNA complementary to any one of (i) the nucleotide sequence shown in SEQ ID NO: 1, (ii) the nucleotide sequences of nucleotide positions 1 to 102 and 142 to 528 of SEQ ID NO: 1, or (iii) the nucleotide sequences of nucleotide positions 1 to 102 and 142 to 582 of SEQ ID NO: 1. These protoporphyrinogen oxidase gene DNAs of the present invention may be collectively referred to as "the present gene DNA."

The above DNA (2) of the present invention is not particularly limited as long as it is a protoporphyrinogen oxidase gene DNA that encodes a protein having an activity of imparting acifluorfen resistance to an organism and having protoporphyrinogen oxidase activity, and contains a nucleotide sequence in which one or several nucleotides are deleted, substituted, or added in any one of (i) the nucleotide sequence shown in SEQ ID NO: 1, (ii) the nucleotide sequences of nucleotide positions 1 to 102 and 142 to 528 of SEQ ID NO: 1, or (iii) the nucleotide sequences of nucleotide positions 1 to 102 and 142 to 582 of SEQ ID NO: 1. However, the following can be preferably exemplified: a protoporphyrinogen oxidase gene DNA that encodes a protein having an activity of imparting acifluorfen resistance to an organism and having protoporphyrinogen oxidase activity, and containing a nucleotide sequence in which one or several nucleotides are deleted, substituted, or added in the nucleotide sequence shown in SEQ ID NO: 1; a protoporphyrinogen oxidase gene DNA that encodes a protein having an activity of imparting acifluorfen resistance to an organism and having protoporphyrinogen oxidase activity, contains a nucleotide sequence in which one or several nucleotides are deleted, substituted, or added in the nucleotide sequences of nucleotide positions 1 to 102 and 142 to 528 of SEQ ID NO: 1, and contains a nucleotide sequence composed of any 30 to (multiple of three only), preferably 36 to 42 (multiple of three only), and more preferably 39 nucleotides between the nucleotide sequence corresponding to said nucleotide sequence of nucleotide positions 1 to 102 and the nucleotide sequence corresponding to said nucleotide sequence of nucleotide positions 142 to 528; a protoporphyrinogen oxidase gene DNA that encodes a protein having an activity of imparting acifluorfen resistance to an organism and having protoporphyrinogen oxidase activity, contains a nucleotide sequence in which one or several nucleotides are deleted, substituted, or added in the nucleotide sequences of nucleotide positions 1 to 102 and 142 to 582 of SEQ ID NO: 1, and contains a nucleotide sequence composed of any 30 to 48 (multiple of three only), preferably 36 to 42 (multiple of three only), and more preferably 39 nucleotides between the nucleotide sequence corresponding to the nucleotide sequence of nucleotide positions 1 to 102 and the nucleotide sequence corresponding to the nucleotide sequence of nucleotide positions 142 to 582. Herein, the nucleotide sequence corresponding to the nucleotide sequences of nucleotide positions m to n means a nucleotide sequence in which one or several nucleotides are deleted, substituted, or added in the nucleotide sequence of nucleotide positions m to n.

The above "nucleotide sequence in which one or several nucleotides are deleted, substituted, or added" means a nucleotide sequence in which any number of nucleotides, for example, 1 to 20, preferably 1 to 15, more preferably 1 to 10, even preferably 1 to 5, and most preferably 1 to 3 nucleotides are deleted, substituted, or added.

For example, DNA containing a nucleotide sequence in which several nucleotides are deleted, substituted, or added (mutant DNA) can be prepared by using any methods known to a person of skill in the art (e.g., chemical synthesis, genetic engineering procedure, mutagenesis, etc.). Specifically, mutant DNAs can be obtained by introducing a mutation into the DNA containing the nucleotide sequence shown in SEQ ID NO: 1 by methods such as a contact with a mutagenic agent, radiation of ultraviolet ray, or genetic engineering procedure. Site specific mutagenesis, which is a technique of genetic engineering, is useful because it allows introduction of a specific mutation into a specific site and it can be performed according to a method described in, e.g., Molecular Cloning: A Laboratory Manual, 2nd Ed., Cold Spring Harbor Laboratory Press, Cold Spring Harbor, N.Y., 1989 (hereinafter referred to as Molecular Cloning 2nd ed.) Expression of this mutant DNA by using an appropriate expression system allows acquisition of proteins containing an amino acid sequence in which one or several amino acids are deleted, substituted, or added.

The "DNA that hybridizes under stringent conditions" means a DNA obtained by performing colony hybridization method, plaque hybridization method, or southern blot hybridization method using a nucleic acid such as DNA or RNA as a probe. Specifically exemplified is a DNA identified by performing a hybridization using a filter, to which colony- or plaque-derived DNAs or fragments of said DNAs are fixed, in the presence of 0.7 to 1.0 M NaCl at 65° C. and subsequent filter washing at 65° C. using about 0.1 to 2×SSC solution (composition of 1×SSC solution is 150 mM sodium chloride and 15 mM sodium citrate). Hybridizations can be performed according to a method described in Molecular Cloning 2nd ed., etc.

Examples of the DNA that hybridizes under stringent conditions include a DNA having homology of above a certain level to a nucleotide sequence of the probe DNA. Preferred examples of the DNA include, for example, a DNA having homology of 60% or more, preferably 70% or more, more preferably 80% or more, even preferably 90% or more, particularly preferably 95% or more, and most preferably 98% or more to any of the following nucleotide sequences: the nucleotide sequence shown in SEQ ID NO: 1; the nucleotide sequences of nucleotide positions 1 to 102 and 142 to 528 of SEQ ID NO: 1; or the nucleotide sequences of nucleotide positions 1 to 102 and 142 to 582 of SEQ ID NO: 1. Here, in the present invention, "homology of X % or more to the nucleotide sequences of nucleotide positions s to t and u to v" means that homology is X % or more to a nucleotide sequence containing the nucleotide sequences of nucleotide positions s to t and nucleotide positions u to v in this order and a nucleotide sequence composed of any 30 to 48 (multiples of three only), preferably 36 to 42 (multiples of three only), and more preferably 39 nucleotides between the nucleotide sequences of nucleotide positions s to t and nucleotide positions u to v. Further, preferred examples of the DNA that hybridizes under stringent conditions include a DNA that encodes an amino acid sequence having a homology of 20% or more, preferably 45% or more, more preferably 54% or more, even preferably 65% or more, further more preferably 80% or more, even more preferably 90% or more, and most preferably 95% or more to any of the following amino acid sequences: the amino acid sequence shown in SEQ ID NO: 2; the amino acid sequences of amino acid positions 1 to 34 and 48 to 176 of SEQ ID NO: 2; or the amino acid sequences of amino acid positions 1 to 34 and 48 to 193 of SEQ ID NO: 2.

The present invention is also directed to a method for using the present DNA as a protoporphyrinogen oxidase gene. The term "using as a protoporphyrinogen oxidase gene" refers to, for example, use in a reaction in which the present DNA is artificially expressed in vitro or in vivo and the expression product protoporphyrinogen oxidase is put into contact with its substrate protoporphyrinogen IX to produce a reaction product protoporphyrin IX. The finding that the expression products of the present DNAs have protoporphyrinogen oxidase activity is a whole new finding first shown in the present invention. With the use of the present DNA as a protoporphyrinogen oxidase gene, for example, acifluorfen resistance can be imparted to an organism not having acifluorfen resistance. Further, the term "artificially expressed" in the method of the present invention for converting protoporphyrinogen IX into protoporphyrin IX by contacting the protoporphyrinogen IX with an expression product artificially expressed from the present DNA, refers to an artificial expression in vitro or in vivo and does not include, for example, non-artificial expression in a cyanobacterial cell.

A method for isolating a present protein or a present gene DNA is not particularly limited and the present proteins or the present gene DNAs may be obtained using a commonly known method such as molecular genetic methods or enzymatic methods. However, to isolate a gene DNA encoding a protoporphyrinogen oxidase having low homology to known protoporphyrinogen oxidases, it is preferred to use a method for isolating a protoporphyrinogen oxidase gene, including the steps of: introducing an *Arabidopsis* protoporphyrinogen oxidase gene into cyanobacterium; disrupting a cyanobacterium gene by using a transposon; selecting a protoporphyrinogen oxidase gene-disrupted mutant strain; identifying the disrupted protoporphyrinogen oxidase gene; and isolating the disrupted protoporphyrinogen oxidase gene.

A source organism may be an acifluorfen non-resistant organism, but preferred is an acifluorfen resistant organism. Hereinbelow, a method using an acifluorfen resistant organism as a source will be described.

Prior to mutagenesis, protoporphyrinogen oxidase gene from an organism related to a source organism is introduced into the source organism and the protoporphyrinogen oxidase gene from the related organism is expressed in the source organism so that the source organism can grow even when the protoporphyrinogen oxidase of the source organism becomes disrupted. Further, a protoporphyrinogen oxidase derived from the related organism that is confirmed not to show acifluorfen resistance is used. Next, mutagenesis using a transposon is performed to the source organism. The mutants obtained are screened by acifluorfen (diphenyl ether herbicide). The source organism shows resistance to acifluorfen but the protoporphyrinogen oxidase from the related organism does not (i.e., it is sensitive). Therefore, the source (protoporphyrinogen oxidase deficient strain) into which the protoporphyrinogen oxidase gene from the related organism is introduced shows sensitivity to acifluorfen. Thus, mutant strains showing normal growth in the absence of the acifluorfen treatment while showing acifluorfen sensitivity when treated with acifluorfen are selected. For example, the gene can be identified by analyzing the strain showing acifluorfen sensitivity for the transposon insertion site with a method described in Example 3, etc. In this way, the source-derived gene encoding protoporphyrinogen oxidase that shows acifluorfen resistance can be isolated.

In the present invention, an organism used as a source of protoporphyrinogen oxidase gene is preferably an organism having an enzyme showing low homology to known protoporphyrinogen oxidases. In the present invention, the gene showing low homology to known protoporphyrinogen oxidase means specifically, for example, a gene having a homology of less than 20% to Tobacco PPX1 gene (Genbank accession Y13465) at amino acid level. In the present invention, an organism used as a source of the protoporphyrinogen oxidase gene is preferably a prokaryote, more preferably cyanobacterium, and most preferably a glucose resistant strain of *Synechocystis* (*Synechocystis* sp. PCC6803) because this strain is easy to obtain and deal with. These bacterial strains can be easily obtained from, for example, the Institute Pasteur. Culture of this strain can be performed according to a commonly known method. It is preferable, however, to culture under continuous light at 30° C. with BG11 culture medium (Hihara Y, et al. Plant Physiol (1998) 117: pp. 1205) adjusted to the final concentration of 5 mM.

A method for obtaining or preparing a present gene DNA is not particularly limited. The present gene DNA can be isolated from, for example, a genomic DNA library of an organism such as *Synechocystis* PCC6803 or other cyanobacterium by using proper primers or probes designed based on the nucleotide sequence information shown in SEQ ID NO: 1 or the amino acid sequence information shown in SEQ ID NO: 2 disclosed herein. Alternatively, they can be prepared by chemical synthesis according to the conventional methods. In addition, acquisition and cloning, etc., of genomic DNA can be carried out according to conventional methods. Methods to screen the genomic DNA library for the present gene DNA include, for example, conventional methods commonly used by a person of skill in the art (e.g., a method described in Molecular Cloning 2nd ed.). Further, mutant genes or homologous genes can be isolated by screening other organisms, etc., under appropriate conditions by using a DNA fragment having a nucleotide sequence shown in SEQ ID NO: 1 or a part thereof for a DNA containing a nucleotide sequence having high homology to said DNA. Alternatively, it can be also prepared by the aforementioned method for generating a mutant DNA.

The recombinant vector of the present invention is not particularly limited as long as it is a vector into which a present gene DNA is incorporated. The recombinant vector of the present invention can be constructed by appropriately introducing the present gene DNA into an expression vector. For example, a structure carrying the present gene DNA linked downstream of a proper promoter can be preferably exemplified. As an expression vector, those able to replicate itself independently in its host cell or able to be incorporated into a chromosome of its host cell is preferred. Further, an expression vector containing genes of a regulatory sequence or a transcription factor, such as a promoter or a terminator, relevant to the expression of a gene of the present invention can be used preferably.

Examples of an expression vector for bacteria include known or commercially available vectors such as pUC lines (e.g., pUC118 (TaKaRa) and pUC19 [Gene, 33, 103 (1985)]), pGEM lines (e.g., pGEMEX-1 (Promega)), pKK223-2 (Pharmacia), pBluescriptII SK(+), and pBluescriptII SK(−) (Stratagene).

Examples of a promoter for bacteria include, for example, T7 phage promoter, trp promoter (P trp), lac promoter (P lac), recA promoter, λPL promoter, λPR promoter, lpp promoter, PSE promoter, SP01 promoter, SP02 promoter, and penP promoter.

Examples of an expression vector for plant cells include pIG121-Hm [Plant Cell Report, 15, 809-814 (1995)], pBI121 [EMBO J. 6, 3901-3907 (1987)], pLAN411, and pLAN421 (Plant Cell Reports 10 (1991) 286-290). Further, examples of a promoter for plants include cauliflower mosaic virus 35S promoter (Mol. Gen. Genet (1990) 220, 389-392), a promoter of alcohol dehydrogenase derived from maize (Maydica 35 (1990) 353-357), and a promoter of IRE gene derived from *Arabidopsis* (Japanese Laid-Open Patent Application No. 2000-270873).

The transformant of the present invention is not limited as long as it is a transformant into which the above vector of the present invention is incorporated. Examples of hosts include microorganisms (such as bacteria), plants, and animals. Among them, microorganisms and plants are preferred. Specific examples of bacteria include bacteria belonging to the genera *Escherichia, Pseudonocardia, Streptomyces, Bacillus, Streptococcus*, and *Staphylococcus*. Further, specific examples of plants include *Arabidopsis*, Tobacco, maize, rice, family of wheat (such as wheat and barley), and potatoes (such as white potato).

Examples of a method for introducing the above recombinant vector of the present invention into a host microorganism include methods described in many standard laboratory manuals such as Molecular Cloning 2nd ed. (e.g., electroporation, transduction, or transformation). Further, examples of a method for introducing said recombinant vector of the present invention include particle gun method, electroporation method, and *Agrobacterium* method.

A transformant, preferably a transformed plant, into which the recombinant vector of the present invention is introduced is thought to have acifluorfen resistance. Herein, the "transformant having acifluorfen resistance" means a transformant whose acifluorfen resistance is increased compared with the resistance before the introduction of the recombinant vector of the present invention. The increase in acifluorfen resistance of the transformant can be evaluated by, for example, investigating whether LC 50 value of acifluorfen to the transformant is increased at 48 hours after the introduction of the recombinant vector compared with the value before the introduction of the recombinant vector. Particularly, when the organism is a plant, increase in acifluorfen resistance of the plant can be investigated by, for example, confirming decrease in degree of etiolation, browning, or desiccation in the plant appropriately expressing the recombinant vector in the plant, compared with the plant before the appropriate expression of the recombinant vector when a particular amount of acifluorfen is applied to the cultivation soil, or it can be investigated by confirming increase in amount of acifluorfen application per unit of area required to cause the same degree of etiolation, browning, or desiccation in the plant appropriately expressing the recombinant vector in the plant, compared with the plant before the appropriate expression of the recombinant vector. Further, degree of improvement in acifluorfen resistance is not particularly limited but it is preferred to be an increase by preferably 1.1 times or more, more preferably 1.5 times or more, even more preferably 2 times or more, and most preferably 3 times or more either in LC 50 value of acifluorfen to the organism at 48 hours later or in amount of acifluorfen application per unit area required to cause the same level of etiolation, browning, or desiccation than that before the introduction of the recombinant vector.

The present protein can be prepared in large quantity by, for example, culturing a transformant of the present invention in an appropriate culture medium to produce and accumulate the present protein in the culture, and then collecting the present protein from said culture. Further, in case of a transformed plant, when acifluorfen is sprayed as agricultural chemical/herbicide, the transformed plant aimed to be grown can grow but acifluorfen-sensitive weeds are killed so that the transformed plant aimed to be grown can be selectively grown.

For a transgenic plant of the present invention, improvement in photosynthetic capacity is preferred although it is not required, and improvement in photosynthetic capacity in the presence of acifluorfen is more preferred. The transformed plant of the present invention is expected to be improved in its photosynthetic capacity because it expresses much protoporphyrinogen oxidase. Improvement in photosynthetic capacity can be confirmed by comparing photosynthetic capacity of the host plant before the introduction of the recombinant vector of the present invention and photosynthetic capacity of the transformed plant after the introduction. Improvement in photosynthetic capacity can be confirmed by, for example, comparing photosynthetic rates calculated from measurements obtained by using a transpiration and photosynthesis measuring system or comparing dry weight of plants cultured under the same conditions for a certain period.

A transformant according to the present invention can be used for a method for evaluating inhibitory activity against protoporphyrinogen oxidase. Examples of said method include, but are not limited to, an evaluating method including the steps of: (1) culturing the host of said transformant in the presence of a test substance and recording its growth curve; (2) culturing said transformant in the presence of the same test substance as in step (1) and recording its growth curve; and (3) comparing the growth curves obtained in steps (1) and (2).

In addition, a transformant of the present invention can also be used for a screening method for a protoporphyrinogen oxidase inhibitor. Examples of said screening method include the same method as the above evaluation method.

Acifluorfen is one of diphenyl ether herbicides. Since the present proteins have activity of imparting acifluorfen resistance to an organism, they would also have an activity of imparting to an organism a resistance against other diphenyl ether herbicides similar in mechanism of action. The same would also apply to the present protoporphyrinogen oxidase and the transformants of the present invention.

Next, a method for isolating a gene encoding a protein having a certain function (e.g., protoporphyrinogen oxidase) from a specific organism (e.g., cyanobacterium) will be explained. This method for isolating a gene includes the following steps of (1) to (5):

(1) generating a transformant by introducing into the specific organism a gene encoding a protein complementing the certain function, wherein the gene is derived from an organism other than the specific organism;

(2) generating a mutant strain of the transformant by randomly disrupting genes of the transformant;

(3) selecting a mutant strain disrupted in the gene encoding the protein having the certain function either by using an agent that acts on the protein complementing the certain function but does not act on the protein having the certain function, or by changing culture conditions;

(4) identifying the disrupted gene encoding the protein having the certain function; and (5) isolating the disrupted gene encoding the protein having the certain function.

This method is especially effective as a gene isolation technique when a protein from other species that is homologous to a known protein (for example, *Arabidopsis*-derived protoporphyrinogen oxidase) can not be found in the gene database of the other species (e.g., cyanobacterium-derived protoporphyrinogen oxidase).

Examples of above mutagenesis include a mutagenesis treating a cell with an agent such as ethyl methanesulfonate (EMS), N-methyl-N-nitro-N-nitrosoguanidine (NTG), 2,6-diaminopurine (DAP), or the like, and a mutagenesis treating a cell with ultraviolet ray. However, a mutagenesis using a transposome, which allows introduction of a mutation at the gene level, can be preferably exemplified. Transposomes are complexes of transposon and transposase and provide easy introduction of a mutation at the gene level into a variety of microorganisms (Hoffman, L. M., Jendrisak, J. J., Meis, R. J., Coryshin, I. Y. and Rezhikof, S. W., Genetica, 108, 19-24 (2000)). For example, as a method using a transposome, a method using EZ::TN™ <KAN-2> Tnp Transposome (EPI-CENTRE), etc., is known.

Mutagenesis methods using a transposon are known in the art as a powerful tool for gene analysis. Gene-disrupted mutants can be selected by, for example, using a specific antibiotic resistance marker introduced by a transposon.

Further screening of the obtained gene-disrupted mutants by using an agent acting on a protein complementing the certain function but not acting on a protein having the certain function, or by changing culture conditions, allows selection of a mutant in which a gene encoding a protein having the certain function is disrupted. The nucleotide sequences adjacent to the transposon can be determined using, for example, the chain termination method (Sanger F. S. et al., Proc. Natl. Acad. Sci., USA, 75:5463-5467 (1977)). This analysis of transposon tag insertion site allows identification of the disrupted gene encoding the protein having the certain function.

Preferred examples of the above "agent that acts on a protein complementing the certain function but does not act on a protein having the certain function" include acifluorfen (diphenyl-ether type), pyraflufen-ethyl (phenylpyrazole type), and flumioxazine (dicarboximido type), which act on *Arabidopsis*-derived protoporphyrinogen oxidase but do not act on cyanobacterium-derived protoporphyrinogen oxidase.

Incidentally, heme and chlorophyll are synthesized from a common precursor δ-aminolevulinic acid (ALA). In plants, *E. coli*, etc., ALA is synthesized via the three-step reaction called "C5 pathway" including the steps of: (1) production of glutamyl-tRNA from glutamic acid by the action of glutamyl-tRNA synthase; (2) production of glutamate 1-semialdehyde from the produced glutamyl-tRNA by the action of glutamyl-tRNA reductase; and (3) production of ALA from the produced glutamate 1-semialdehyde by the action of glutamate-1-semialdehyde aminomutase. In animals or bacteria belonging to the genus *Agrobacterium*, in contrast, ALA is synthesized via the one-step reaction called "C4 pathway" from succinyl CoA and glycine by the action of ALA synthase. As described above, bacteria belonging to the genus *Agrobacterium* synthesize ALA via "C4 pathway" and the enzyme ALA synthase is known to exist although the gene thereof is not identified. In such a case, the ALA synthase gene from bacteria belonging to the genus *Agrobacterium* can be identified by coinfecting the bacteria belonging to the genus *Agrobacterium* with genes encoding plant-derived glutamyl-tRNA synthase, glutamyl-tRNA reductase, and glutamate 1-semialdehyde aminomutase, randomly disrupting a gene in the transformed bacteria belonging to the genus *Agrobacterium* using a transposon or the like to generate mutant strains, selecting the mutant strains for a mutant strain that grows in the absence of gabaculine, which is an inhibitor of glutamate 1-semialdehyde aminomutase, and is killed in the presence of gabaculine, and analyzing the transposon tag insertion site in the selected mutant strain. Therefore, examples of aforedescribed "agent that acts on a protein complementing the certain function but does not act on a protein having the certain function" include gabaculine which acts on glutamate 1-semialdehyde aminomutase from a plant or *E. coli*, and does not act on δ-aminolevulinic acid (ALA) synthase from an animal or bacterium belonging to the genus *Agrobacterium*.

Furthermore, examples of a selection method via changing culture conditions for a mutant strain in which a gene encoding a protein having a certain function is disrupted include: as a selection method based on temperature conditions, for example a method including culturing gene-disrupted mutants at normal culturing temperature and at high (or low) temperature to select mutants showing difference in growth; as a selection method based on light conditions, for example, a method including culturing gene-disrupted mutants under normal light conditions and under high (or low) light conditions to select mutants showing difference in growth; and as a selection method based on pH conditions, for example, a method including culturing gene-disrupted mutants at normal pH conditions and at high (or low) pH conditions to select mutants showing difference in growth.

The present invention will be further described in detail with reference to the following Examples. However, the technical scope of the present invention will not be limited by these Examples.

Example 1

Introduction of *Arabidopsis*-Derived Protoporphyrinogen Oxidase Gene into Cyanobacterium Total RNA was extracted from rosette leaves of *Arabidopsis* by using RNeasy RNA extraction kit (Qiagen). Poly(A)+ mRNA was purified from the total RNA by using a conventional method. The poly(A)+ mRNA was used as a template for synthesis of cDNA using ReverTra-Plus-Kit (TOYOBO). An *Arabidopsis* protoporphyrinogen oxidase gene (1.6 kbp) was amplified by PCR using the synthesized cDNA as a template, a primer ATHPPDX.AseIf (SEQ ID NO: 3) containing a restriction enzyme AseI site, a primer ATHPPDX.r (SEQ ID NO: 4), and TaKaRa LA Taq polymerase (TAKARA). Then the PCR product was digested with AseI. The PCR was performed with 28 cycles of denaturation (94° C., 30 s), annealing (52° C., 45 s), and extension (72° C., 120 s).

pFS10, which can be used for transformation of cyanobacteria and has kanamycin resistance gene, was used as a vector (Jansson, et al. Methods Enzymol (1998) 297: pp 166). The pFS10 vector was digested with restriction enzymes NdeI and HincII and ligated to the aforementioned PCR product of the protoporphyrinogen oxidase gene to generate a recombinant vector. This recombinant vector was transformed into *E. coli* (JM109) by heat shock method, and transformants were then selected on LB agar plate containing kanamycin. Emerged colony was cultured in LB liquid medium containing kanamycin and plasmid was purified from the culture. In a later step of mutagenesis using transposon, kanamycin resistance will be used as a selectable marker. Therefore, removal of kanamycin resistance gene and introduction of another antibiotic resistance gene (chloramphenicol resistance gene) are required.

Primary PCR was carried out with primers Chloram.r (SEQ ID NO: 5) and SPE2Xba1.r (SEQ ID NO: 6) having an XbaI site, Pyrobest Taq polymerase (TAKARA), and pFS10 vector as a template. The PCR was performed with 25 cycles of denaturation (98° C., 10 s), annealing (55° C., 45 s), and extension (72° C., 30 s), and an approximately 500-bp PCR product was yielded. Next, secondary PCR was carried out using the chloramphenicol resistance gene as a template, with the obtained PCR product, a primer Chloram.Xba1.f (SEQ ID NO: 7), and Pyrobest Taq polymerase (TAKARA). The PCR was performed with 25 cycles of denaturation (98° C., 10 s), annealing (50° C., 45 s), and extension (72° C., 90 s). The PCR product which contained a chloramphenicol resistance gene was digested with the restriction enzyme XbaI.

Meanwhile, the aforementioned recombinant vector constructed by ligating the *Arabidopsis* protoporphyrinogen oxidase gene with pFS10 vector was also digested with XbaI to remove the kanamycin resistance gene and then ligated with the XbaI-digested chloramphenicol resistance gene fragment described above to obtain a new recombinant vector. This recombinant vector was transformed into *E. coli* (JM109) and transformants were then selected on LB agar medium containing chloramphenicol. Emerged colony was cultured in LB liquid medium containing chloramphenicol and plasmid was purified from the culture. *Synechocystis* PCC6803 was transformed with this plasmid to generate a transgenic *Synechocystis* strain expressing *Arabidopsis*-derived protoporphyrinogen oxidase (hereinafter referred to as "AT strain" in some cases). The method of transformation of *Synechocystis* PCC6803 was carried out according to Williams J G. Methods Enzymol (1998) 167: pp 766.

Example 2

Generation of Cyanobacterium Mutant Using a Transposon

Genome extracted from *Synechocystis* PCC6803 was partially digested with Tsp5091 and genomic plasmid library was constructed by using lambda ZAP II vector kit (Stratagene). A transposon was inserted into the genomic plasmid library by using EZ::TNTM<KAN-2> Insertion Kit (Epicentre) according to a manual disclosed by Epicentre. With this transposon tag-inserted genomic plasmid library of *Synechocystis*, AT strain was transformed by homologous recombination to generate *Synechocystis* mutants expressing *Arabidopsis*-derived protoporphyrinogen oxidase.

Example 3

Screening for Cyanobacterium Protoporphyrinogen Oxidase-Deficient Mutants

The *Synechocystis* mutants generated in Example 2 were screened for cyanobacterium protoporphyrinogen oxidase-deficient mutants by using acifluorfen sensitivity as a selectable marker. Specific procedures are described below.

The *Synechocystis* mutants generated in Example 2 were plated on BG11 agar medium containing acifluorfen at a final concentration of 500 μM and cultured statically under continuous radiation by white fluorescent light (light intensity: 30 μmol s$^{-1}$ m$^{-2}$) at 30° C. for two weeks. Culture on acifluorfen-free BG11 agar medium was also carried out in the same way. Based on the results of these cultures, nine mutants that grow in the absence of acifluorfen but are killed in the presence of acifluorfen were selected. Among these nine mutants, a mutant the growth of which was most inhibited was named 3216 mutant and insertion site of the transposon tag was analyzed as described below. The transposon tag was found to be inserted within a putative transcriptional regulatory domain of the protein slr1790.

(Genetic Analysis of Cyanobacterium Mutant)

Two methods were contemplated as a way to determine the insertion site of the transposon tag.

(1) Since a kanamycin resistance gene is introduced as a tag into the used transposon, this antibiotic resistance is used for selecting.

Specifically, DNA is obtained from a mutant and fragmented using a restriction enzyme sequence not included in the kanamycin resistance gene. A vector not containing a kanamycin resistance gene is digested with the same restriction enzyme as used for DNA cleavage. These are ligated and transformed into *E. coli*. Plasmid is purified from a clone which has grown on a medium containing kanamycin and then the sequence is analyzed.

(2) Use of inverse PCR method. DNA is obtained from a mutant as in (1) and fragmented using a restriction enzyme sequence not included in the transposon tag. This is self-ligated (circulated) and subjected to PCR reaction with designed primers toward the outside of the transposon tag. The amplified PCR product is sequenced.

First, the method of (1) using an antibiotic resistance was employed for investigation.

(1) Investigation Using Kanamycin Resistance

<DNA Extraction from Cyanobacterium Mutant>

A cyanobacterium mutant (3216 mutant) was cultured in BG11 liquid medium at 30° C. under light for 12 days. After the culture, cells were collected and DNA was extracted by SDS method. As a result, approximately 800 μg of cyanobacterium mutant's DNA was obtained.

<Digestion with Restriction Enzymes>

Restriction enzymes EcoR1 and Sac1 were used to digest the cyanobacterium mutant DNA and a vector (pUC118), respectively. After the restriction enzyme treatment, fragmented cyanobacterium mutant DNA was purified using a spin column. The vector was treated with alkaline phosphatase in order to avoid self-ligation.

<Ligation>

Average length of the fragments yielded by digestion with the above three restriction enzymes is calculated from a database to be 6 kb and 10 kb for EcoRI and SacI, respectively. In view of the average fragment length, molar ratio of insert/vector was adjusted to 3/1 or 9/1 and ligated at 12° C. for 16 hours.

<Transformation to *E. coli*>

An aliquot of ligation mixture was transformed into *E. coli* (JM109) by heat-shock method, which was then subjected to a selection on kanamycin-containing LB agar medium. As a result, no colony formation was observed on the kanamycin-containing LB agar medium.

Ligation using too excessive an amount of the insert in insert/vector ratio also resulted in the same. The selection method utilizing an antibiotic resistance would be theoretically possible. In this case, however, there would be some problems such as inappropriate conditions of insert/vector ratio. Although there is room for studying the conditions, it was determined to investigate using the inverse PCR method as shown in (2).

(2) Investigation Using Inverse PCR Method

The 3216 mutant, which shows a strong phenotype, was investigated. DNA was obtained as described above and restriction enzymes EcoRI and Kpn1 were used. After restriction enzyme treatment, DNA fragment was purified with a spin column.

<Self-Ligation>

The DNA fragment purified by using a spin column was self-ligated at 12° C. for 16 hours.

<1st and 2nd PCR>

Since there is a concern about amplification of non-specific bands for inverse PCR method, PCR reaction was performed in two steps.

Two sets of primers toward the outside of the transposon tag were designed. For the 2nd PCR, sequence primers included in the kit were used.

```
(1st PCR primers)
                                (SEQ ID NO: 17)
KAN-2-fr (SEQ ID NO: 18)
KAN-2-rev (2nd PCR primers)
                                (SEQ ID NO: 19)
KAN-2FP1

(SEQ ID NO: 20)
KAN-2RP1
```

1st PCR was carried out using a self-ligated genomic fragment as a template. The 1st PCR was performed with 30 cycles of 98° C. for 10 s (denaturation), 55° C. for 30 s (annealing), and 72° C. for 7 min (extension) using primers with a final concentration of 0.5 μM each and EX taq polymerase (Takara).

Final concentrations of the template using the ligation reaction mixture were investigated for three dilutions (1:50, 1:250, and 1:1250). An amount of 5 μl of the PCR products was examined by agarose gel electrophoresis.

The electrophoresis showed amplification of a specific band around 7 kb only when EcoRI-digested fragment was used as a template. The 1st PCR product was purified with a spin column to remove the primers and then used as a template for the 2nd PCR.

The 2nd PCR was performed with 3 cycles of 98° C. for (denaturation), 60° C. for 30 s (annealing), and 72° C. for 5 min (extension), followed by 20 cycles of 98° C. for 10 (denaturation), 58° C. for 30 s (annealing), and 72° C. for 5 min (extension) using primers with a final concentration of 0.5 μM each and EX taq polymerase (Takara).

An amount of 5 μl of the PCR product was examined by agarose gel electrophoresis.

As a result, in accordance with the primer design, amplification of a band was observed at a lower position than the 1st PCR product by several hundred bp. At the same time, however, amplification of non-specific bands was also observed.

<TA Cloning and Plasmid Purification>

The 2nd PCR condition was investigated. However, the amplification of non-specific bands could not be removed. Therefore, the band around 7 kb specifically amplified in the 1st PCR was retrieved from the gel and used as an insert for TA cloning (pGEM-T Easy vector, Promega), which was then transformed into E. coli (JM109) by heat shock method and transformants were selected on LB agar medium containing ampicillin. Four colonies were selected from the colonies that emerged on the plate and were cultured in LB liquid medium containing ampicillin, and then plasmid purification was performed by using mini-prep procedure. Since the insert can be excised from pGEM-T Easy vector by EcoR1 treatment, the purified plasmids were treated with EcoR1 and examined by agarose gel electrophoresis.

The electrophoresis of plasmid 1 and plasmid 2 showed bands around 5 kb, 3 kb (vector), and 1.8 kb. Since total size of the bands derived from the insert was approximately 7 kb, these clones were determined to be clones of interest. Possible cause of yielding three cleaved bands, including the vector-derived band, by EcoR1 treatment of plasmids 1 and 2 is formation of a concatemer instead of circular form at the initial ligation step. This does not affect sequence analysis. Therefore, the plasmid 1 was subjected to sequence reaction.

<Sequencing>

Nucleotide sequence of the plasmid 1 was analyzed by cycle sequencing according to dideoxy method. As sequence primers, KAN-2FP1 and KAN-2RP1 used in the 2nd PCR were employed. Since the sequence primers anneal DNA of transposon tag region, the initial part of obtained sequence data is for the DNA of transposon tag region. An inverted repeat sequence is a 19-bp Transposon Mosaic End Transposase recognition sequence found at the junction of the target DNA and the transposon tag within a transposon-inserted clone. This sequence can be used to distinguish the target from the transposon tag. Transposase-catalyzed transposon insertion generates a 9-bp target site sequence duplication to protect the sides of the inserted transposon.

In view of the above, the obtained sequence was analyzed and transposon tag was found to be inserted between 256677th T and 256685th G (Mosaic end sequence and 9-bp overlapping sequence). This position is not included in ORF region but considered to be a transcriptional regulatory domain of downstream putative protein slr1790 (256698-257279, 193 aa).

Of the nine mutants, which grow in the absence of acifluorfen but are killed in the presence of acifluorfen, the eight mutants other than the 3216 mutant were analyzed in the same way. Transposon tag was inserted into the same gene in all the mutants as the 3216 mutant (slr1790).

Example 4

Generation of Protein Slr1790 Gene-Disrupted Mutant

To determine whether the slr1790 gene (600 bp from 256698 to 257279 of Synechocystis genome) codes protoporphyrinogen oxidase or not, slr1790 gene disruption in Synechocystis PCC6803 was performed by using a recombinant vector which codes a kanamycin resistance gene inserted within the coding region of slr1790. Since cyanobacterium can be transformed by homologous recombination, primers were designed based on the sequence between 700 bp upstream and 600 bp downstream of the slr1790 gene (1.9 kbp from 255999 to 257920 of Synechocystis genome). Sequence including 700 bp upstream and 600 bp downstream of the slr1790 gene was amplified by PCR using DNA extracted from Synechocystis PCC6803 as a template, primers Slr1790 km EcoR1 f (SEQ ID NO: 8) and Slr1790 km Hind3 r (SEQ ID NO: 9), and TaKaRa EX Taq polymerase (Takara) to obtain a PCR product. The PCR was performed with 28 cycles of denaturation (98° C., 10 s), annealing (55° C., 30 s), and extension (72° C., 120 s). Resultant PCR product was ligated to pGEM-T Easy vector (Promega).

The vector including the sequence containing the slr1790 gene was transformed into E. coli (strain JM109) by heat shock method and transformants were selected on LB agar medium containing ampicillin. Emerged colony was cultured in LB liquid medium containing ampicillin and plasmid (pslr1790S) was purified from the culture. Next, PCR was carried out by using the kanamycin resistance gene (1.3 kbp) included in the transposon tag as a template, primers which contain Nhe1 site, Km Nhe1 f (SEQ ID NO: 10) and Km Nhe1 r (SEQ ID NO: 11), and TaKaRa EX Taq polymerase (Takara) to amplify a PCR product containing the kanamycin resistance gene. The PCR was performed with 28 cycles of denaturation (98° C., 10 s), annealing (58° C., 30 s), and extension (72° C., 80 s). Obtained PCR product was digested with Nhe1 and ligated into Nhe1 site at a middle of the slr1790 gene of the a vector. This plasmid was transformed into *E. coli* (JM109) by heat shock method and transformants were selected on LB agar medium containing kanamycin. Emerged colony was cultured in LB liquid medium containing kanamycin, and plasmid (pslr1790SKM) was purified from the culture. This construct for slr1790 gene disruption is shown in FIG. 3. *Synechocystis* PCC6803 was transformed with this plasmid pslr1790SKM and slr1790 gene-disrupted mutants were selected by culturing the resultant transformant on BG11 agar medium containing kanamycin. The transformation of *Synechocystis* PCC6803 was performed according to a method described previously (Williams J G. Methods Enzymol (1998) 167: pp 766).

Example 5

Analysis of Protein Slr1790 Gene-Disrupted Mutant

When protoporphyrinogen oxidase is disrupted, accumulation of protoporphyrinogen IX, which is a substrate, is expected. However, protoporphyrinogen IX is so unstable that it easily reacts with oxygen in the air and is easily oxidized to protoporphyrin IX during extraction process. Therefore, disruption of protoporphyrinogen oxidase can be determined by measuring the amount of protoporphyrin IX after extraction operation in air. Measurement of the amount of protoporphyrin IX for slr1790 gene-disrupted mutant was performed as follows.

The slr1790 gene-disrupted mutant obtained in Example 4 was cultured in 50 ml of aerated BG11 liquid medium using a test tube under continuous light with white fluorescent light (light intensity: 30 µmol s$^{-1}$ m$^{-2}$), at 30° C. for 1 week to obtain culture solution. Pigments containing protoporphyrin IX were extracted from the obtained culture solution by using 90% acetone to obtain pigment extract solution. This pigment extract solution was subjected to HPLC and HPLC analysis was performed using octylsilica column (Waters Symmetry C8 (150×4.6 mm)) and methanol (eluent) under the conditions of flow rate of 1.2 ml/min and column oven set at 40° C. (pump LC-10ATVP and auto sampler SIL-10ADVP are from Shimadzu Corp.). Protoporphyrin IX was monitored using the excitation wavelength of 405 nm and fluorescence wavelength of 633 nm (fluorescence detector RF-10AXL is from Shimadzu Corp.). The result is shown in FIG. 4C. Further, instead of slr1790 gene-disrupted mutant, analysis of *Synechocystis* PCC6803, in which the gene is not disrupted, was performed in the same way and the result is shown in FIG. 4B. Further, chromatogram of protoporphyrin IX sample is shown in FIG. 4A.

Figure 4:
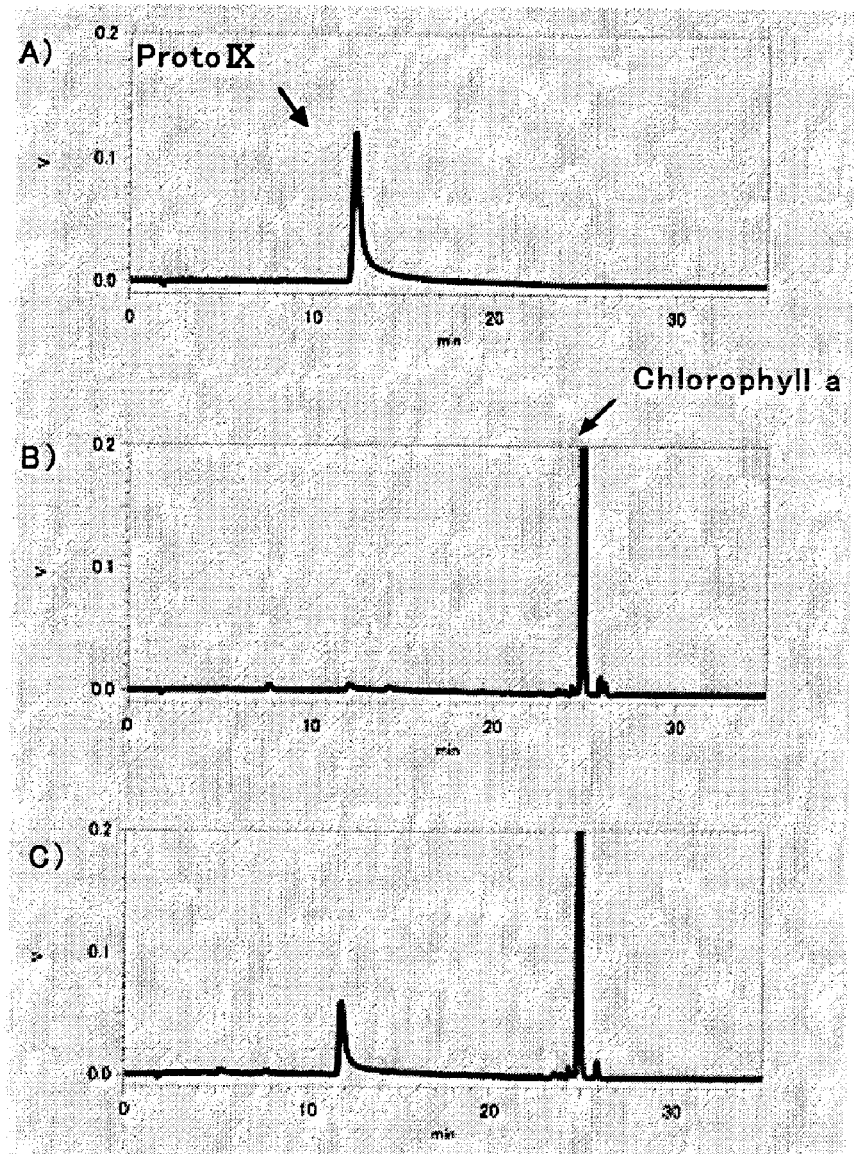
FIG. 4 is a figure showing chromatograms of protoporphyrin IX sample (A), extract of slr1790 gene-disrupted strain (B), and extract of wild type (C).

As shown in FIG. 4, 20 times or more protoporphyrin IX was accumulated in the slr1790 gene-disrupted mutant than in a strain in which the gene is not disrupted. From this and the fact that the unidentified enzyme among the enzymes relating to cyanobacterium metabolism of protoporphyrinogen IX or protoporphyrin IX is only protoporphyrinogen oxidase, it has been revealed that slr1790 codes for protoporphyrinogen oxidase. Also, slr1790 has an extremely low homology to known protoporphyrinogen oxidases. Homologies of known protoporphyrinogen oxidases to slr1790 at amino acid level are shown in Table 3.

TABLE 3

| Known protoporphyrinogen oxidases | Homology to slr1790 (%) |
|---|---|
| Tobacco PPX1 (Genbank accession Y13465) | 12.2 |
| Tobacco PPX2 (Genbank accession Y13466) | 12.5 |
| *Arabidopsis thaliana* PPOX (Genbank accession D83139) | 12.5 |
| *Bacillus subtilis* HemY (Genbank accession M97208) | 13.4 |
| Mouse PPX (Genbank accession D45185) | 13.6 |
| Human PPX (Genbank accession D38537) | 13.6 |
| *Saccharomyces cerevisiae* PPX (Genbank accession 271381) | 11.9 |
| *E.coli* hemG (Genbank accession X68660) | 14.9 |

Example 6

Introduction of Cyanobacterium Protoporphyrinogen Oxidase Slr1790 Into *Arabidopsis*

Figure 5:
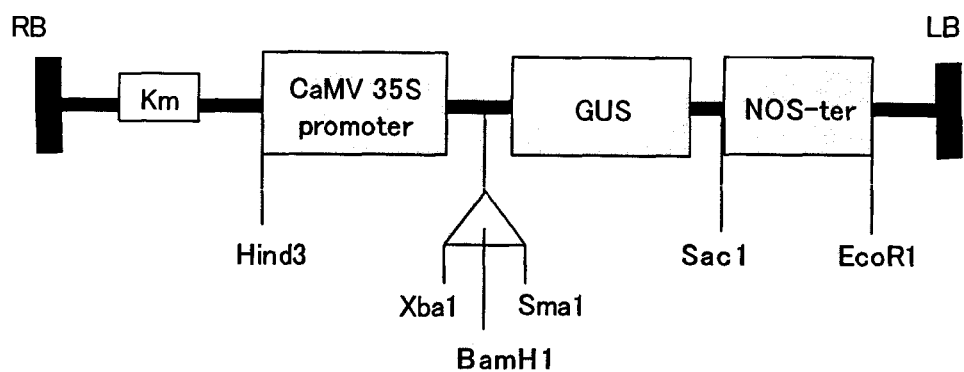
FIG. 5 is a figure showing a schematic view of pBI121.

As an expression vector for plants, pBI121 was used. FIG. 5 shows a schematic view of pBI121.

Plant protoporphyrinogen oxidase is an enzyme existing in chloroplasts and mitochondria. This time, however, chloroplast localization signal of *Arabidopsis*-derived chlorophyll a oxygenase (CAO, Genbank accession BT002075) was linked to the slr1790 gene and introduced in order to express slr1790 in chloroplast. For prediction of localization signal, TargetP (http://www.cbs.dtu.dk/services/TargetP/) was used. Detailed procedure is as follows.

pBI121 vector (14.8 kbp) was treated with restriction enzymes BamH1 and Sac1 to remove a GUS gene (1.9 kbp) and the vector part (12.9 kbp) was purified from gel. Further, using the *Arabidopsis* cDNA obtained in Example 1 as a template, CAO-derived chloroplast localization signal (0.2 kbp) was amplified by PCR using primers BamSma CAO fr. (SEQ ID NO: 12) and Sac CAO rev. (SEQ ID NO: 13) having restriction enzyme BamH1 and Sac1 recognition site, respectively, and KOD-Plus-polymerase (TOYOBO). The PCR was performed with 30 cycles of denaturation (94° C., 15 s), annealing (55° C., 30 s), and extension (68° C., 15 s).

The obtained PCR product was ligated into pTA2 vector having ampicillin resistance (TOYOBO, TA cloning vector for KOD-Plus, 2.9 kbp), then transformed into *E. coli* (JM109) by heat shock method, and transformants were selected on LB agar medium containing ampicillin. Emerged colony was cultured in LB liquid medium containing ampicillin and then plasmid (pTACAO) was purified. Plasmid pTACAO was digested with restriction enzymes BamH1 and Sac1 to excise the chloroplast localization signal, which was then purified from gel. The purified chloroplast localization signal derived from CAO was ligated as an insert into pBI121 vector, from which the GUS gene had been removed in advance. This was transformed into *E. coli* (JM109) and transformants were selected on LB agar medium containing kanamycin. Emerged colony was cultured in LB liquid medium containing kanamycin and then plasmid (pBICAO, 13.1 kbp) was purified. pBICAO was digested with restriction enzyme Sac1 and treated with CIP to avoid self-ligation, and then vector fragment was purified from gel.

Figure 6:
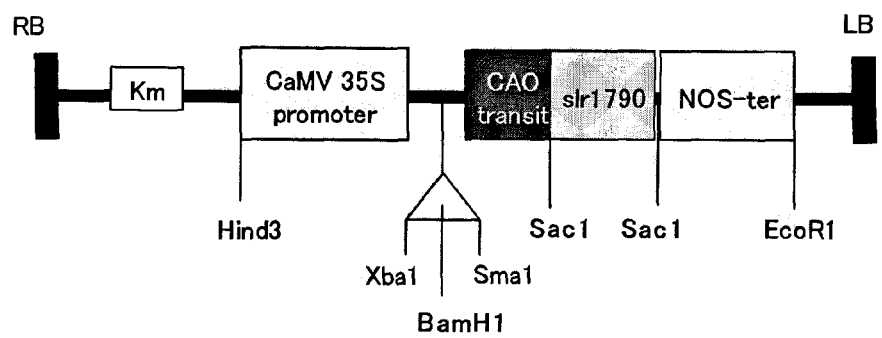
FIG. 6 is a figure showing a schematic view of pBIslr1790.

Next, slr1790 gene (0.6 kbp) was amplified by PCR using genome extracted from *Synechocystis* as a template, primers Sac slr1790fr. (SEQ ID NO: 14) and Sac slr1790 rev. (SEQ ID NO: 15), in which restriction enzyme Sac1 recognition site is included, and KOD-Plus-polymerase (TOYOBO). The PCR was performed with 30 cycles of denaturation (94° C., 15 s), annealing (55° C., 30 s), and extension (68° C., 35 s). The obtained PCR product was ligated into pTA2 vector having ampicillin resistance, then transformed into *E. coli* (JM109) by heat shock method, and transformants were selected on LB agar medium containing ampicillin. Emerged colony was cultured in LB liquid medium containing ampicillin and then plasmid (pTAslr1790Sac) was purified. Plasmid pTAslr1790Sac was digested with the restriction enzyme Sac1 to excise the slr1790 gene, which was then purified from gel. The purified slr1790 gene was ligated as an insert into the pBICAO that had been digested with the restriction enzyme Sac1 in advance, which was then transformed into *E. coli* (JM109) by heat shock method and transformants were selected on LB agar medium containing kanamycin. Emerged colony was cultured in LB liquid medium containing kanamycin and plasmid (pBIslr1790, 13.6 kbp) was purified. Schematic view of pBIslr1790 is shown in FIG. 6.

Next, *Arabidopsis* was transformed by in planta method by using *Agrobacterium tumefaciens* C58 strain in which pBIslr1790 was introduced by freezing method.

*Agrobacterium tumefaciens* C58 strain harboring pBIslr1790 was suspended in 300 mL of transformation buffer (5% sucrose, 0.02% silwetL-77) at a bacterial density of around OD600=0.8–1.0. Next, the above-ground part of pot-planted *Arabidopsis* having buds was soaked in the above mentioned suspension for 30 seconds, and then each pot was covered with a plastic bag for two days. After uncovering, the culture was continued to obtain seeds. The culture was performed in a growth chamber (24 h light, temperature: 22° C., light intensity: 70 $\mu mols^{-1}m^{-2}$). The obtained seeds were sterilized and inoculated on ½ Murashige-Skoog medium containing 35 ppm kanamycin and 0.6% agar [T. Murashige and F. Skoog, Physiol. Plant (1962) 15: pp 473] to obtain transformants (slr lineage). The transformants were transplanted to earth and cultured in a growth chamber to obtain second generation seeds.

Example 7

Resistance Effect of Transformants Against Acifluorfen

For second generation of transformants in which the introduction of the gene was confirmed, acifluorfen resistance was investigated.

Introduction of the gene was confirmed with the following method.

A region approximately 2 mm in diameter was harvested from a leaf of each transformed *Arabidopsis* slr lineage grown to 1 to 2 cm in height in a growth chamber and genomic DNA was extracted. PCR amplification was performed by using this genomic DNA as a template, primers AtCAO-tra-up (SEQ ID NO: 16) and Sac slr1790 rev. (SEQ ID NO: 15), which anneal N terminus and C terminus of the introduced gene, respectively, and Taq DNA polymerase (SIGMA). Presence of bands was examined by agarose gel electrophoresis. The PCR was performed with 40 cycles of denaturing (95° C., 30 s), annealing (55° C., 45 s), and extension (72° C., 60 s).

For transformants in which gene introduction was confirmed, acifluorfen resistance effect was tested. Acifluorfen was prepared as emulsion to contain 4% of effective component by mixing and solubilizing dimethylformamide and polyoxyethylene sorbitan surfactant. This was diluted with water to make the final concentration of acifluorfen 10 µM, 5 µl of which was dropped using a micropippet onto leaves of *Arabidopsis* wild type and transformed *Arabidopsis* slr lineage, in which gene introduction was confirmed, both grown to 1 to 2 cm in height in a growth chamber.

Study was continued until 7 days after the treatment with the chemicals and degree of necrosis was evaluated by eye (on a 0 to 5 scale, 0 means no effect). Results at 7 days after treatment are shown in Table 4. The result shows acifluorfen resistance in slr1790-introduced *Arabidopsis* in comparison with *Arabidopsis* wild type.

TABLE 4

Resistance of slr1790-introduced *Arabidopsis* against acifluorfen (7 days after treatment)

|  | Acifluorfen Treatment (10 µM) |
|---|---|
| *Arabidopsis* Wild Type | 4 |
| slr 52 | 1 |
| slr 146 | 1 |

Evaluation was done by eye on a 0 to 5 scale, with 5 meaning complete death and 0 meaning no effect.

Example 8

Test for Inhibitory Potency of Protoporphyrinogen Oxidase Inhibitor

The AT strain obtained in Example 1 and ATΔslr1790 strain, in which slr1790 gene was disrupted by the method described in Example 4, were used. Aforedescribed BG11 liquid medium was employed. With a view to preventing reverse mutation or loss of the gene, either chloramphenicol or kanamycin was added to the medium at a final concentration of 25 µM for the AT strain and ATΔslr1790 strain, respectively, because a chloramphenicol resistance gene is introduced with protoporphyrinogen oxidase into AT strain and a kanamycin resistance gene is introduced into ATΔslr1790 strain when disrupting the gene. AT strain and ATΔslr1790 strain were precultured with shaking in BG11 liquid medium, collected during the growth phase, and suspended in fresh BG11 liquid medium supplemented with an antibiotic so that A730 became 0.1, which was used for investigation.

An active pharmaceutical ingredient of a test chemical was dissolved in DMSO and added to wells so that final concentration of agent became from $1.0 \times 10^{-4}$ M to $1.0 \times 10^{-9.5}$ M for each well (the final concentration of DMSO is 0.5%). The test includes shaking culture using a 96-well plate in a scale of 100 µl in each well at 30° C. of incubation temperature under 1000 lux of light intensity. Turbidity was measured 6 days after the start of the test and compared with solvent sample to calculate pI50 value.

$$pI50\ value = -\log(\text{concentration to inhibit 50\% activity} (M))$$

(Activity of Herbicidal Treatment)

Seeds of *Amaranthus lividus* were sowed on the surface of soil filled in a pot (200 cm²) followed by covering with a little soil and then grown to 5 to 10 cm of plant length in a greenhouse. Each of water-diluted test chemical solutions was sprayed to foliage part of *Amaranthus lividus* with a small spray in an amount corresponding to the spray amount of 1000 litter/ha to achieve predetermined amount of agent. Cultivation was carried out in a greenhouse. Then herbicidal effect on *Amaranthus lividus* was examined two weeks after the treatment according to an examination criterion below. Results are shown in herbicide index in the below table.

TABLE 5

| Examination criterion | |
|---|---|
| Herbicide rate | Herbicide index |
| 0% | 0 |
| 20-29% | 2 |
| 40-49% | 4 |
| 60-69% | 6 |
| 80-89% | 8 |
| 100% | 10 |

Values 1, 3, 5, 7, and 9 indicate the intermediate value of and 2, 2 and 4, 4 and 6, 6 and 8, and 8 and 10 respectively.

TABLE 6

| | pI50 Value | | Herbicidal activity (foliage treatment) (herbicide index for |
|---|---|---|---|
| Test chemicals | AT strain | ATΔslr1790 strain | *Amaranthus lividus*, 16 g ai/ha) |
| acifluorfen | 4> | 4.5 | 7 |
| pyraflufenethyl | 4> | 6.6 | 10 |
| flumioxazine | 4> | 6.7 | 10 |
| diquat | 5.2 | 5 | — |

TABLE 7

| Test chemicals |
|---|
| Protoporphyrinogen oxidase inhibitor |
| acifluorfen (diphenyl-ether type) |
| pyraflufen-ethyl (phenylpyrazole type) |
| flumioxazine (dicarboxyimido type) |

TABLE 7-continued

| Test chemicals |
|---|
| Non-protoporphyrinogen oxidase inhibitor |
| diquat |

ATΔslr1790 strain showed sensitivity to agents other than acifluorfen, which is a diphenyl ether-type inhibitor of protoporphyrinogen oxidase. This means protoporphyrinogen oxidase inhibitors generally show inhibitory effect against ATΔslr1790 strain. Further, tendency of pI50 value of each test chemical for ATΔslr1790 strain reflects activities of each foliage treatment and can be used to evaluate the effect of inhibitory activity against protoporphyrinogen oxidase.

Example 9

Screening Method for a Protoporphyrinogen Oxidase-Specific Inhibitor Compound

From the Example above, AT strain did not show sensitivity to protoporphyrinogen oxidase inhibitor while ATΔslr1790 does. On the other hand, non-protoporphyrinogen oxidase inhibitor showed inhibitory activity against both AT strain and ATΔslr1790 strain to similar extent. In this way, by comparing inhibitory effect of a chemical against AT strain and ATΔslr1790 strain, inhibitory effect of each test chemical against protoporphyrinogen oxidase is determined.

Since the protoporphyrinogen oxidase of the present invention has a significantly different structure from known ones, it is expected to be applied to selection of new protoporphyrinogen oxidase inhibitor herbicides. Further, the protoporphyrinogen oxidase of the present invention is expected to be applied to breeding of photosynthetic plants having resistance to a protoporphyrinogen oxidase inhibitor herbicide or plants having resistance to stressful environment. Moreover, even in a case where a protein homologous to a known protein can not be found in a gene database of other species, the method of the present invention for isolating a gene can provide an effective method to isolate the gene of other species.

What is claimed is:

1. A method for isolating a cyanobacterium protoporphyrinogen oxidase gene, comprising the steps of:

i. introducing an *Arabidopsis* protoporphyrinogen oxidase gene into a cyanobacterium;

ii. disrupting a cyanobacterium gene by using a transposon;

iii. selecting a protoporphyrinogen oxidase gene-disrupted mutant strain;

iv. identifying the disrupted protoporphyrinogen oxidase gene; and v. isolating the disrupted protoporphyrinogen oxidase gene, wherein the gene encodes an amino acid sequence having 54% or more homology to SEQ ID No:2.

2. The method according to claim 1, wherein the introducing step comprises transforming the cyanobacterium with a vector.

3. The method according to claim 1, wherein the transposon comprises a specific antibiotic resistance marker.

4. The method of claim 3, wherein the marker is a kanamycin resistance gene.

5. The method according to claim 1, wherein the selecting step is performed using an agent or changing a culture condition.

6. The method according to claim 5, wherein the agent is selected from the group consisting of acifluorfen, pyraflufen-ethyl and flumioxazine.

7. The method according to claim 6, wherein the agent is acifluorfen and step (iii) consists of selecting mutant strains showing normal growth in the absence of the acifluorfen treatment while showing acifluorfen sensitivity when treated with acifluorfen.

8. The method according to claim 1, wherein the identifying step comprises identifying the nucleotide sequences adjacent to the transposon to determine the transposon tag insertion site.

9. The method according to claim 1, wherein the cyanobacterium is selected from the group consisting of *Synechocystis, Anabaena, Gloeobacter, Prochlorococcus* and *Synechococcus.*

10. The method of claim 9, wherein the cyanobacterium is selected from the group consisting of *Synechocystis* PCC6803, *Anabaena* PCC7120, *Gloeobacter violaceus* PCC7421, *Prochlorococcus marinus* SS120, *Prochlorococcus marinus* MIT9313, *Prochlorococcus marinus* MED4 and *Synechococcus* WH8102.

11. The method according to claim 1, wherein the gene encodes a protoporphyrinogen oxidase.

* * * * *

SEQUENCE LISTING

```
<160> NUMBER OF SEQ ID NOS: 30

<210> SEQ ID NO 1
<211> LENGTH: 582
<212> TYPE: DNA
<213> ORGANISM: Synechocystis sp. PCC6803

<400> SEQUENCE: 1
atggcctact actggtttaa agccttccac ttgattggca ttgttgtttg gtttgctgga      60
ttattttatt tagtgcgtct ttttgtctat cacgccgagg cagaccagga gccggaacca     120
gctaaaacta tcctcaaaaa acagtatgag ttgatggaaa agcggcttta caacatcatc     180 actaccccccg gcatggtagt tacggtggct atggcgatcg gtctcatttt cacagaaccc     240
gaaattctca aatccggctg gctccacatc aaactcacct ttgtggcgtt actgttgctt     300
taccatttct attgtggtcg ggtgatgaaa aagctagccc aggggggaatc ccaatggagt     360 gggcaacagt tccgggcttt aaatgaggca ccgactattt tgctcgtggt gattgtccta     420
ctggcggtgt ttaagaataa tttgcccctg gatgcgacca cttggttaat tgtagctttg     480
```

```
gttattgcca tggctgcttc gattcaactc tacgctaaaa aacgtcgccg ggaccaagca    540
ctattaacgg aacagcaaaa agcggcttct gctcagaatt ag                      582
```

<210> SEQ ID NO 2
<211> LENGTH: 193
<212> TYPE: PRT
<213> ORGANISM: Synechocystis sp. PCC6803

<400> SEQUENCE: 2

```
Met Ala Tyr Tyr Trp Phe Lys Ala Phe His Leu Ile Gly Ile Val Val
1               5                   10                  15

Trp Phe Ala Gly Leu Phe Tyr Leu Val Arg Leu Phe Val Tyr His Ala
            20                  25                  30

Glu Ala Asp Gln Glu Pro Glu Pro Ala Lys Thr Ile Leu Lys Lys Gln
        35                  40                  45

Tyr Glu Leu Met Glu Lys Arg Leu Tyr Asn Ile Ile Thr Thr Pro Gly
    50                  55                  60

Met Val Val Thr Val Ala Met Ala Ile Gly Leu Ile Phe Thr Glu Pro
65                  70                  75                  80

Glu Ile Leu Lys Ser Gly Trp Leu His Ile Lys Leu Thr Phe Val Ala
                85                  90                  95

Leu Leu Leu Leu Tyr His Phe Tyr Cys Gly Arg Val Met Lys Lys Leu
            100                 105                 110

Ala Gln Gly Glu Ser Gln Trp Ser Gly Gln Gln Phe Arg Ala Leu Asn
        115                 120                 125

Glu Ala Pro Thr Ile Leu Leu Val Val Ile Val Leu Leu Ala Val Phe
    130                 135                 140

Lys Asn Asn Leu Pro Leu Asp Ala Thr Thr Trp Leu Ile Val Ala Leu
145                 150                 155                 160

Val Ile Ala Met Ala Ala Ser Ile Gln Leu Tyr Ala Lys Lys Arg Arg
                165                 170                 175

Arg Asp Gln Ala Leu Leu Thr Glu Gln Gln Lys Ala Ala Ser Ala Gln
            180                 185                 190

Asn
```

<210> SEQ ID NO 3
<211> LENGTH: 29
<212> TYPE: DNA
<213> ORGANISM: Artificial Sequence
<220> FEATURE:
<223> OTHER INFORMATION: Synthetic Construct - Primer ATHPPOX.Ase1f

<400> SEQUENCE: 3

```
ggggattaat ggagttatct cttctccgt                                      29
```

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct - Primer ATHPPOX.r

<400> SEQUENCE: 4

```
ttacttgtaa gcgtaccgtg                                                20
```

<210> SEQ ID NO 5
<211> LENGTH: 37
<212> TYPE: DNA
<213> ORGANISM: Artificial Sequence
<220> FEATURE:

-continued

<223> OTHER INFORMATION: Synthetic Construct - Primer Chloram.r

<400> SEQUENCE: 5
gctaaccgtt tttatcacct gggggggcacc ttattt                          37

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct - Primer SPE2Xba1.r

<400> SEQUENCE: 6
tgtttctaga taatcctggt c                                          21

<210> SEQ ID NO 7
<211> LENGTH: 28
<212> TYPE: DNA
<213> ORGANISM: Artificial Sequence
<220> FEATURE:
<223> OTHER INFORMATION: Synthetic Construct - Chloram.Xba1.f

<400> SEQUENCE: 7
ggtctagatg atgtccggcg gtgctttt                                   28

<210> SEQ ID NO 8
<211> LENGTH: 30
<212> TYPE: DNA
<213> ORGANISM: Artificial Sequence
<220> FEATURE:
<223> OTHER INFORMATION: Synthetic Construct - Primer Slr1790km EcoR1 f

<400> SEQUENCE: 8
ggggaattct gcttgcatca atatggtggc                                 30

<210> SEQ ID NO 9
<211> LENGTH: 29
<212> TYPE: DNA
<213> ORGANISM: Artificial Sequence
<220> FEATURE:
<223> OTHER INFORMATION: Synthetic Construct - Primer Slr1790km Hind3 r

<400> SEQUENCE: 9
gggaagctta ccctggagat ccactggtt                                  29

<210> SEQ ID NO 10
<211> LENGTH: 30
<212> TYPE: DNA
<213> ORGANISM: Artificial Sequence
<220> FEATURE:
<223> OTHER INFORMATION: Synthetic Construct - Primer Km Nhe1 f

<400> SEQUENCE: 10
ggggctagcg cgaagaactc cagcatgaga                                 30

<210> SEQ ID NO 11
<211> LENGTH: 32
<212> TYPE: DNA
<213> ORGANISM: Artificial Sequence
<220> FEATURE:
<223> OTHER INFORMATION: Synthetic Construct - Primer Km Nhe1 r

<400> SEQUENCE: 11
ggggctagca gcttcacgct gccgcaagca ct                              32

<210> SEQ ID NO 12

-continued

```
<211> LENGTH: 48
<212> TYPE: DNA
<213> ORGANISM: Artificial Sequence
<220> FEATURE:
<223> OTHER INFORMATION: Synthetic Construct - Primer BamSma CAO fr.

<400> SEQUENCE: 12
gaggatcccc gggtggtcag tcccttatga acgccgccgt gtttagtc                 48

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct - Primer Sac CAO rev.

<400> SEQUENCE: 13
ttacttgtaa gcgtaccgtg                                                20

<210> SEQ ID NO 14
<211> LENGTH: 32
<212> TYPE: DNA
<213> ORGANISM: Artificial Sequence
<220> FEATURE:
<223> OTHER INFORMATION: Synthetic Construct - Primer Sac slr1790fr.

<400> SEQUENCE: 14
ccgagctcgc ctactactgg tttaaagcct tc                                  32

<210> SEQ ID NO 15
<211> LENGTH: 29
<212> TYPE: DNA
<213> ORGANISM: Artificial Sequence
<220> FEATURE:
<223> OTHER INFORMATION: Synthetic Construct - Primer Sac slr1790 rev

<400> SEQUENCE: 15
ccgagctcct aattctgagc agaagccgc                                      29

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct - Primer AtCAO-tra-up

<400> SEQUENCE: 16
aacgccgccg tgtttagtcc                                                20

<210> SEQ ID NO 17
<211> LENGTH: 22
<212> TYPE: DNA
<213> ORGANISM: Artificial Sequence
<220> FEATURE:
<223> OTHER INFORMATION: Synthetic Construct - KAN-2-fr

<400> SEQUENCE: 17
ggcctgttga acaagtctgg aa                                             22

<210> SEQ ID NO 18
<211> LENGTH: 24
<212> TYPE: DNA
<213> ORGANISM: Artificial Sequence
<220> FEATURE:
<223> OTHER INFORMATION: Synthetic Construct - KAN-2-rev

<400> SEQUENCE: 18
```

```
ggcgtttccc gttgaatatg gctc                                            24
```

<210> SEQ ID NO 19
<211> LENGTH: 25
<212> TYPE: DNA
<213> ORGANISM: Artificial Sequence
<220> FEATURE:
<223> OTHER INFORMATION: Synthetic Construct - KAN-2FP1

<400> SEQUENCE: 19

```
acctacaaca aagctctcat caacc                                           25
```

<210> SEQ ID NO 20
<211> LENGTH: 25
<212> TYPE: DNA
<213> ORGANISM: Artificial Sequence
<220> FEATURE:
<223> OTHER INFORMATION: Synthetic Construct - KAN-2RP1

<400> SEQUENCE: 20

```
gcaatgtaac atcagagatt ttgag                                           25
```

<210> SEQ ID NO 21
<211> LENGTH: 180
<212> TYPE: PRT
<213> ORGANISM: Anabaena sp. PCC 7120

<400> SEQUENCE: 21

```
Met Val Trp Phe Ala Gly Leu Phe Tyr Leu Val Arg Leu Phe Ile Tyr
1               5                   10                  15

His Val Glu Ala Asn Gln Glu Pro Glu Pro Ala Arg Thr Ile Leu Lys
            20                  25                  30

Asn Gln Tyr Gln Ile Met Glu Lys Arg Leu Tyr Asn Ile Ile Thr Thr
        35                  40                  45

Pro Gly Met Leu Val Thr Val Ala Met Ala Ile Gly Leu Val Ser Thr
    50                  55                  60

Glu Pro Glu Val Leu Lys Gln Gly Trp Leu His Phe Lys Leu Leu Cys
65                  70                  75                  80

Val Ala Leu Leu Leu Gly Tyr His His Tyr Cys Gly Arg Leu Met Lys
                85                  90                  95

Lys Leu Ala Ala Asp Glu Cys Arg Trp Ser Ser Gln Gln Leu Arg Ala
            100                 105                 110

Leu Asn Glu Ala Pro Thr Val Met Leu Val Val Ile Val Met Leu Ala
        115                 120                 125

Val Phe Lys Asn Asn Leu Pro Thr Asp Leu Thr Ala Trp Leu Ile Phe
    130                 135                 140

Ala Leu Ile Ile Phe Met Ala Val Thr Ile Gln Leu Tyr Ala Lys Lys
145                 150                 155                 160

Arg Arg Leu Asp Lys Glu Lys Leu Thr Ala Gln Ile Gly Gln Ile Pro
                165                 170                 175

Gln Glu Gln Ser
            180
```

<210> SEQ ID NO 22
<211> LENGTH: 190
<212> TYPE: PRT
<213> ORGANISM: Gloeobacter violaceus PCC 7421

<400> SEQUENCE: 22

```
Met Ala Tyr Leu Trp Phe Lys Ala Phe His Ile Val Gly Phe Val Thr
1               5                   10                  15
```

Trp Phe Ala Gly Leu Phe Tyr Leu Val Arg Leu Phe Ile Tyr His Val
            20                  25                  30

Glu Ala Asn Glu Gln Pro Glu Ala Ala Arg Ala Ile Leu Lys Lys Gln
        35                  40                  45

Tyr Glu Ile Met Glu Lys Arg Leu Leu Asn Ile Ile Thr Thr Pro Gly
    50                  55                  60

Met Val Leu Thr Val Ala Met Ala Val Gly Met Leu Val Val Gln Pro
65                  70                  75                  80

Asp Trp Leu Lys Ala Gly Trp Leu His Ile Lys Leu Thr Leu Val Val
                85                  90                  95

Leu Leu Met Gly Tyr His Phe Tyr Cys Met Arg Leu Arg Thr Gln Leu
            100                 105                 110

Ala Ala Gly Thr Cys Arg Trp Gly Pro Lys Gln Leu Arg Ala Leu Asn
        115                 120                 125

Glu Ala Pro Thr Ile Leu Leu Val Thr Ile Val Leu Leu Ala Val Phe
    130                 135                 140

Lys Asn Asp Leu Pro Thr Asp Ala Thr Ala Trp Ile Val Phe Gly Leu
145                 150                 155                 160

Val Ile Ser Phe Ala Val Thr Ile Gln Leu Tyr Ala Arg Lys Arg Arg
                165                 170                 175

Leu Asp Lys Glu Lys Gln Leu Ala Ser Gln Gly Gly Gln Gln
            180                 185                 190

<210> SEQ ID NO 23
<211> LENGTH: 188
<212> TYPE: PRT
<213> ORGANISM: Prochlorococcus marinus SS120

<400> SEQUENCE: 23

Met Ser Leu Pro Ala Glu Ser Tyr Leu Trp Leu Lys Thr Leu His Ile
1               5                   10                  15

Ile Gly Val Val Val Trp Phe Ala Gly Leu Phe Tyr Leu Val Arg Leu
            20                  25                  30

Phe Ile Tyr His Val Glu Ala Asp Glu Leu Glu Ser Asp Ile Lys Phe
        35                  40                  45

Ala Phe Val Asn Gln Tyr Ser Leu Met Glu Arg Arg Leu Ala Asn Ile
    50                  55                  60

Ile Thr Thr Pro Gly Met Ile Leu Ala Val Ser Met Ala Ile Gly Leu
65                  70                  75                  80

Leu Ile Tyr Asn Pro Ser Trp Leu Glu Gln Thr Trp Met Gln Val Lys
                85                  90                  95

Leu Phe Pro Val Phe Leu Leu Leu Ile Tyr His Ile Phe Cys Tyr Arg
            100                 105                 110

Leu Met Ser Ser Leu Ala Lys Gly Glu Cys Lys Trp Ser Gly Gln Gln
        115                 120                 125

Leu Arg Ile Leu Asn Glu Leu Pro Thr Leu Phe Leu Val Ile Val Val
    130                 135                 140

Met Leu Val Val Phe Lys Asn Asn Phe Pro Thr Ser Ala Ala Thr Trp
145                 150                 155                 160

Leu Ile Val Phe Leu Val Ile Phe Met Ala Leu Ser Ile Gln Leu Tyr
                165                 170                 175

Ala Arg Phe Arg Arg Ile Asn Lys Glu Lys Gln Ile
            180                 185

<210> SEQ ID NO 24

-continued

```
<211> LENGTH: 195
<212> TYPE: PRT
<213> ORGANISM: Prochlorococcus marinus MIT9313

<400> SEQUENCE: 24

Met Thr Phe Pro Pro Glu Ala Tyr Leu Trp Phe Lys Thr Leu His Ile
1               5                   10                  15

Val Gly Val Val Val Trp Phe Ala Gly Leu Phe Tyr Leu Val Arg Leu
                20                  25                  30

Phe Ile Tyr His Val Glu Ala Ala Asp Leu Glu Pro Thr Val Lys Lys
            35                  40                  45

Ala Phe Glu Glu Gln Tyr Thr Leu Met Glu Arg Arg Leu Ala Asn Ile
    50                  55                  60

Ile Thr Thr Pro Gly Met Ile Leu Ala Val Ser Met Ala Val Gly Leu
65                  70                  75                  80

Leu Ile Thr Gln Pro Ser Trp Leu Asn Gln Ala Trp Met Gln Ala Lys
                85                  90                  95

Leu Ala Leu Val Ala Gly Leu Ile Ala Tyr His Ile Phe Cys Tyr Arg
            100                 105                 110

Leu Met Gly Gln Leu Asn Arg Gly Glu Cys Ser Trp Ser Gly Arg Gln
        115                 120                 125

Leu Arg Ala Leu Asn Glu Leu Pro Thr Leu Phe Leu Val Leu Val Val
    130                 135                 140

Met Leu Val Val Phe Lys Asn Gln Phe Pro Thr Gly Ala Ala Thr Trp
145                 150                 155                 160

Leu Ile Val Gly Leu Val Leu Phe Met Ala Ala Ser Ile Gln Phe Tyr
                165                 170                 175

Ala Arg Trp Arg Arg Leu Arg Leu Ser Arg Gln Leu Glu Ser Pro Leu
            180                 185                 190

Asn Asn Gly
        195

<210> SEQ ID NO 25
<211> LENGTH: 192
<212> TYPE: PRT
<213> ORGANISM: Synechococcus sp. WH8102

<400> SEQUENCE: 25

Met Thr Leu Pro Pro Glu Ala Tyr Leu Trp Phe Lys Thr Leu His Ile
1               5                   10                  15

Val Gly Val Val Val Trp Phe Ala Gly Leu Phe Tyr Leu Val Arg Leu
                20                  25                  30

Phe Ile Tyr His Val Glu Thr Ala Glu Leu Ala Glu Asp Leu Gln Gln
            35                  40                  45

Pro Phe Arg Asp Gln Tyr Ser Leu Met Glu Lys Arg Leu Ala Asn Ile
    50                  55                  60

Ile Thr Thr Pro Gly Met Val Val Ala Val Ser Met Ala Ile Gly Leu
65                  70                  75                  80

Leu Val Ala Gln Pro Ser Trp Leu Gln Gln Gly Trp Met His Ala Lys
                85                  90                  95

Leu Gly Phe Val Ala Gly Leu Leu Ala Tyr His Val Ala Cys Tyr Arg
            100                 105                 110

Leu Met Gly Gln Leu Gln Ala Gly Thr Cys Arg Leu Ser Gly Lys Gln
        115                 120                 125

Leu Arg Ala Leu Asn Glu Leu Pro Thr Leu Leu Leu Val Ile Val Val
    130                 135                 140
```

```
Met Leu Val Val Phe Lys Ser Gln Phe Pro Thr Gly Ala Ala Thr Trp
145                 150                 155                 160

Phe Ile Val Ala Leu Val Phe Met Ala Ala Ser Ile Gln Phe Tyr
                165                 170                 175

Ala Arg Trp Arg Arg Leu Arg Ala Glu Ala Gln Ala Val Thr Gly Ser
            180                 185                 190
```

<210> SEQ ID NO 26
<211> LENGTH: 199
<212> TYPE: PRT
<213> ORGANISM: Prochlorococcus marinus MED4

<400> SEQUENCE: 26

```
Met Val Ile Val Tyr Glu Leu Tyr Phe Ile Asn Leu Ser Ser Glu Ala
1               5                   10                  15

Tyr Leu Trp Phe Lys Ser Leu His Ile Ile Gly Val Ile Val Trp Phe
                20                  25                  30

Ser Gly Leu Phe Tyr Leu Val Arg Leu Phe Ile Tyr His Glu Glu Ser
            35                  40                  45

Arg Thr Met Gln Asp Asp Leu Lys Ile Ala Phe Asn Asp Gln Tyr Ser
        50                  55                  60

Leu Met Glu Lys Arg Leu Ala Asn Ile Ile Thr Thr Pro Gly Met Ile
65                  70                  75                  80

Leu Ala Leu Ser Met Ala Ile Cys Leu Val Ile Met Gln Pro Gly Trp
                85                  90                  95

Leu Ser Glu Lys Trp Leu Gln Ile Lys Ile Ser Phe Val Leu Gly Leu
            100                 105                 110

Val Ile Tyr His Val Tyr Cys Tyr Lys Ile Met Asn Ser Leu Gln Asn
        115                 120                 125

Gly Thr Ser Lys Ile Ser Ala Lys Asn Leu Arg Leu Leu Asn Glu Leu
130                 135                 140

Pro Thr Leu Leu Leu Phe Val Ile Val Leu Leu Val Ile Phe Lys Asn
145                 150                 155                 160

Asn Phe Pro Thr Ser Ile Ala Thr Trp Ser Val Phe Gly Leu Ile Ile
                165                 170                 175

Phe Met Leu Leu Ser Ile Gln Leu Tyr Ala Lys Ile Arg Lys Lys Asn
            180                 185                 190

Glu Glu Ser Leu Lys Asn Gly
            195
```

<210> SEQ ID NO 27
<211> LENGTH: 140
<212> TYPE: PRT
<213> ORGANISM: Pseudomonas aeruginosa

<400> SEQUENCE: 27

```
Met Tyr Met Trp Leu Lys Ala Phe His Ile Ile Ala Val Val Cys Trp
1               5                   10                  15

Phe Ala Gly Leu Phe Tyr Leu Pro Arg Leu Phe Val Tyr His Ala Met
                20                  25                  30

Ser Glu Asp Gln Thr Ser Arg Glu Arg Phe Cys Val Met Glu Arg Lys
            35                  40                  45

Leu Tyr Arg Gly Ile Met Met Pro Ser Met Leu Ala Thr Leu Val Leu
        50                  55                  60

Gly Leu Trp Met Leu Tyr Leu Thr Pro Gly Trp Leu Ser Gln Gly Trp
65                  70                  75                  80

Leu His Ala Lys Leu Thr Leu Val Val Leu Leu Ile Gly Tyr His His
```

```
                        85                  90                  95
Ala Cys Gly Ala Met Leu Lys Arg Phe Ala Arg Gly Glu Pro Gly Arg
            100                 105                 110

Ser His Val Phe Tyr Arg Trp Phe Asn Glu Val Pro Val Leu Phe Leu
            115                 120                 125

Leu Leu Ile Val Leu Leu Val Val Leu Lys Pro Phe
            130                 135                 140

<210> SEQ ID NO 28
<211> LENGTH: 148
<212> TYPE: PRT
<213> ORGANISM: Helicobacter pylori

<400> SEQUENCE: 28

Met Gly Phe Leu Asn Gly Tyr Phe Leu Trp Val Lys Ala Phe His Val
1               5                   10                  15

Ile Ala Val Ile Ser Trp Met Ala Ala Leu Phe Tyr Leu Pro Arg Leu
            20                  25                  30

Phe Val Tyr His Ala Glu Asn Ala His Lys Lys Glu Phe Val Gly Val
            35                  40                  45

Val Gln Ile Gln Glu Lys Lys Leu Tyr Ser Phe Ile Ala Ser Pro Ala
        50                  55                  60

Met Gly Phe Thr Leu Ile Thr Gly Ile Leu Met Leu Leu Ile Glu Pro
65                  70                  75                  80

Thr Leu Phe Lys Ser Gly Gly Trp Leu His Ala Lys Leu Ala Leu Val
                85                  90                  95

Val Leu Leu Leu Ala Tyr His Phe Tyr Cys Lys Lys Cys Met Arg Glu
            100                 105                 110

Leu Glu Lys Asp Pro Thr Arg Arg Asn Ala Arg Phe Tyr Arg Val Phe
            115                 120                 125

Asn Glu Ala Pro Thr Ile Leu Met Ile Leu Ile Val Ile Leu Val Val
        130                 135                 140

Val Lys Pro Phe
145

<210> SEQ ID NO 29
<211> LENGTH: 165
<212> TYPE: PRT
<213> ORGANISM: Agrobacterium tumefaciens

<400> SEQUENCE: 29

Met Arg Ala Gly Val Ala Leu Gly Val Phe Ala Ala Phe Ile Ala Leu
1               5                   10                  15

Leu Phe Tyr Ala Asp Pro Ala Asp Leu Tyr Leu Trp Ile Lys Ala Leu
            20                  25                  30

His Ile Ile Ala Val Ile Ser Trp Met Ala Ala Ile Phe Tyr Leu Pro
            35                  40                  45

Arg Leu Phe Ile Tyr His Thr Asp Ala Pro Val Gly Ser Gln Gln Ser
        50                  55                  60

Glu Thr Phe Lys Val Met Glu Gln Arg Leu Ile Arg Val Ile Met Asn
65                  70                  75                  80

Pro Ala Met Met Ile Ser Trp Thr Leu Gly Leu Tyr Leu Ala Trp Ser
                85                  90                  95

Val Tyr Gly Phe Ser Gly Gly Trp Leu His Ala Lys Ile Gly Leu Val
            100                 105                 110

Leu Leu Leu Thr Ala Thr His Val Tyr Phe Ser Arg Ser Ala Lys Arg
            115                 120                 125
```

-continued

```
Phe Ala Arg Asp Glu Asn Thr Arg Pro Ala Arg His Trp Arg Leu Met
    130                 135                 140

Asn Glu Val Pro Thr Val Leu Met Ile Leu Ile Val Ile Leu Val Val
145                 150                 155                 160

Val Lys Pro Phe Gly
                165

<210> SEQ ID NO 30
<211> LENGTH: 154
<212> TYPE: PRT
<213> ORGANISM: Brucella melitensis

<400> SEQUENCE: 30

Met Leu Gly Val Trp Ala Leu Phe His Val Asn Pro Thr Asp Ala Tyr
1               5                   10                  15

Leu Trp Val Lys Ala Leu His Val Ile Ala Val Ile Ser Trp Met Ala
            20                  25                  30

Gly Met Leu Tyr Leu Pro Arg Leu Phe Val Tyr His Cys Ser Ala Gln
        35                  40                  45

Pro Gly Ser Val Thr Ser Glu Thr Phe Lys Val Met Glu Lys Arg Leu
    50                  55                  60

Leu Arg Phe Ile Ile Asn Pro Ala Met Val Val Thr Trp Ile Thr Gly
65                  70                  75                  80

Leu Trp Met Ala Trp Glu Ile Phe Gly Phe Gln Gly Gly Trp Leu His
                85                  90                  95

Ala Lys Leu Leu Leu Val Val Leu Met Ser Gly Val His Gly Tyr Leu
            100                 105                 110

Ser Lys Ser Thr Arg Ile Phe Ala Glu Asp Arg Asn Met Ser Ser Ala
        115                 120                 125

Lys His Trp Arg Ile Ile Asn Glu Val Pro Thr Val Leu Met Ile Leu
    130                 135                 140

Ile Val Ile Leu Ala Ile Val Lys Pro Phe
145                 150
```